(12) United States Patent
Lee et al.

(10) Patent No.: US 12,601,002 B2
(45) Date of Patent: Apr. 14, 2026

(54) METHOD FOR PREDICTING AND IMPROVING TREATMENT RESPONSE TO INTESTINAL MICROBIOME-BASED CANCER IMMUNOTHERAPY AND METHOD FOR SCREENING FOR CANDIDATE PREBIOTICS

(71) Applicant: INDUSTRY-ACADEMIC COOPERATION FOUNDATION, YONSEI UNIVERSITY, Seoul (KR)

(72) Inventors: In Suk Lee, Seoul (KR); Sang Jun Ha, Seoul (KR); Chan Yeong Kim, Seoul (KR); Hye Ryun Kim, Seoul (KR); Beung Chul Ahn, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 622 days.

(21) Appl. No.: 18/004,390

(22) PCT Filed: Jun. 30, 2021

(86) PCT No.: PCT/KR2021/008284
§ 371 (c)(1),
(2) Date: Jan. 5, 2023

(87) PCT Pub. No.: WO2022/010169
PCT Pub. Date: Jan. 13, 2022

(65) Prior Publication Data
US 2023/0235376 A1 Jul. 27, 2023

(30) Foreign Application Priority Data
Jul. 6, 2020 (KR) ........................ 10-2020-0082994

(51) Int. Cl.
*C12Q 1/25* (2006.01)
*C12Q 1/02* (2006.01)
(52) U.S. Cl.
CPC .................................... *C12Q 1/025* (2013.01)

(58) Field of Classification Search
None
See application file for complete search history.

(56) References Cited
U.S. PATENT DOCUMENTS
2020/0129569 A1 4/2020 Wargo et al.

FOREIGN PATENT DOCUMENTS

| | | |
|---|---|---|
| JP | 2016204355 A | 12/2016 |
| KR | 1020180011262 A | 1/2018 |
| WO | 2018115519 A1 | 6/2018 |
| WO | 2019086540 A1 | 5/2019 |
| WO | 2019191390 A2 | 10/2019 |

OTHER PUBLICATIONS

Chen et al., "Fecal microbiota transplantation in cancer management: Current status and perspectives", International Journal of Cancer, vol. 145, 2019, pp. 2021-2031.
Dan et al., "Altered gut microbial profile is associated with abnormal metabolism activity of Autism Spectrum Disorder", Gut Microbes, vol. 11, No. 5, 2020, pp. 1246-1267.
International Search Report for PCT Application No. PCT/KR2021/008284, dated Nov. 4, 2021, 7 pages (4 pages of Official copy and 3 pages of English Translation).
Stancu et al., "Gut Microbiome and the Response to Immunotherapy in Cancer", Discoveries Journals, vol. 6, No. 3, Jul.-Sep. 2018, 9 pages.

*Primary Examiner* — Michelle F. Paguio Frising
(74) *Attorney, Agent, or Firm* — ROTHWELL, FIGG, ERNST & MANBECK, P.C.

(57) ABSTRACT
Provided are a method for predicting a treatment response to cancer immunotherapy, the method comprising a step of evaluating, from feces isolated from a patient, the enrichment of a strain of the order TANB77 according to GTDB phylogenetic classification or taxa belonging to the order TANB77, and a step of predicting a treatment response of the patient to cancer immunotherapy on the basis of the enrichment of the order TANB77 or the taxa; a probiotics composition for improving a treatment response; a fecal microbiota transplantation composition; and a method for screening for candidate prebiotics by using same.

13 Claims, 18 Drawing Sheets

(a)

(b)

| GTDB Taxonomy | Enriched in | LDA |
|---|---|---|
| d__Bacteria;p__Firmicutes_A;c __Clostridia;o__TANB77 | Responder | 3.40 |
| d__Bacteria;p__Firmicutes_A;c __Clostridia;o__Lachnospirales;f__Lachnospiraceae;g __Faecalicatena;s__Faecalicatena torques | Responder | 3.29 |
| d__Bacteria;p__Firmicutes_A;c __Clostridia;o__TANB77;f__CAG_508;g__CAG_269 | Responder | 3.21 |
| d__Bacteria;p__Synergistota;c__Synergistia;o __Synergistales;f__Dethiosulfovibrionaceae | Responder | 2.62 |
| d__Bacteria;p__Desulfobacterota_A;c__Desulfovibrionia;o __Desulfovibrionales;f__Desulfovibrionaceae;g__Desulfovibrio;s __Desulfovibrio piger | Responder | 2.23 |

FIG. 4A

| GTDB Taxonomy | Enriched in | LDA |
|---|---|---|
| d__Bacteria;p__Firmicutes_A;c__Clostridia;o__Peptostreptococcales;f__Peptostreptococcaceae;g__Intestinibacter;s__Intestinibacter bartlettii | Non-responder | 2.14 |
| d__Bacteria;p__Firmicutes_A;c__Clostridia;o__Peptostreptococcales;f__Peptostreptococcaceae;g__Intestinibacter | Non-responder | 2.19 |
| d__Bacteria;p__Proteobacteria;c__Gammaproteobacteria;o__Enterobacterales;f__Enterobacteriaceae;g__Morganella;s__Morganellamorganii | Non-responder | 2.27 |
| d__Bacteria;p__Firmicutes_A;c__Clostridia;o__Oscillospirales;f__Oscillospiraceae;g__CAG_103;s__CAG_103 sp000432375 | Non-responder | 2.48 |
| d__Bacteria;p__Firmicutes_A;c__Clostridia;o__Oscillospirales;f__Oscillospiraceae;g__Negativibacillus | Non-responder | 2.85 |
| d__Bacteria;p__Firmicutes_A;c__Clostridia;o__Oscillospirales;f__Oscillospiraceae;g__CAG_83;s__CAG_83 sp000431575 | Non-responder | 2.91 |
| d__Bacteria;p__Firmicutes_A;c__Clostridia;o__Oscillospirales;f__Oscillospiraceae;g__CAG_103 | Non-responder | 3.31 |

FIG. 4B

| Taxon | Enriched in | LDA | P-value |
|---|---|---|---|
| d_Bacteria;p_Firmicutes_A;c_Clostridia;o_Lachnospirales;f_CAG-274;g_OTU_3439 | Responder | 2.08 | 0.0017 |
| d_Bacteria;p_Firmicutes_A;c_Clostridia;o_TANB77;f_CAG-508;g_OTU_3050 | Responder | 2.12 | 0.0092 |
| d_Bacteria;p_Firmicutes_A;c_Clostridia;o_TANB77 | Responder | 2.40 | 0.0125 |
| d_Bacteria;p_Proteobacteria;c_Gammaproteobacteria;o_Burkholderiales;f_Burkholderiaceae;g_CAG-521;s_OTU_5310 | Responder | 2.48 | 0.0171 |
| d_Bacteria;p_Desulfobacterota_A;c_Desulfovibrionia;o_Desulfovibrionales;f_Desulfovibrionaceae;g_Mailhella;s_OTU_5403 | Responder | 5.44 | 0.0186 |
| d_Bacteria;p_Firmicutes_A;c_Clostridia;o_4C28d-15;f_UBA3700;g_OTU_2955 | Responder | 2.53 | 0.0272 |
| d_Bacteria;p_Firmicutes_A;c_Clostridia;o_4C28d-15;f_UBA3700 | Responder | 2.17 | 0.0318 |
| d_Bacteria;p_Firmicutes_A;c_Clostridia;o_TANB77;f_CAG-508;g_CAG-273;s_sp000438355 | Responder | 4.22 | 0.0335 |
| d_Bacteria;p_Firmicutes_I;c_Bacilli_A;o_Thermoactinomycetales;f_Thermoactinomycetaceae;g_Risungbinella | Responder | 2.06 | 0.0411 |
| d_Bacteria;p_Firmicutes_I;c_Bacilli_A;o_Thermoactinomycetales;f_Thermoactinomycetaceae | Responder | 2.06 | 0.0411 |
| d_Bacteria;p_Firmicutes_I;c_Bacilli_A;o_Thermoactinomycetales;f_Thermoactinomycetaceae;g_Risungbinella;s_Risungbinella mossiliensis | Responder | 2.06 | 0.0411 |
| d_Bacteria;p_Firmicutes_A;c_Clostridia;o_TANB77;f_CAG-508;g_OTU_3026 | Responder | 3.91 | 0.0432 |

FIG. 4C

| Taxon | enriched in | Log2 (Fold-abundance) | P-value |
|---|---|---|---|
| d__Bacteria;p__Proteobacteria;c__Alphaproteobacteria;o__Rs-D84;f__Rs-D84;g__Rs-D84;s__OTU_5368 | Non-responder | -3.94 | 0.0016 |
| d__Bacteria;p__Bacteroidota;c__Bacteroidia;o__Bacteroidales;f__Muribaculaceae;g__CAG-873;s__OTU_4953 | Non-responder | -2.14 | 0.0038 |
| d__Bacteria;p__Actinobacteriota;c__Coriobacteriia;o__Coriobacteriales;f__Coriobacteriaceae;g__Collinsella;s__OTU_4397 | Non-responder | -2.46 | 0.0043 |
| d__Bacteria;p__Firmicutes_A;c__Clostridia;o__Oscillospirales;f__Butyricicoccaceae;g__Butyricicoccus;s__OTU_2599 | Non-responder | -2.44 | 0.005 |
| d__Bacteria;p__Proteobacteria;c__Gammaproteobacteria;o__Enterobacterales;f__Enterobacteriaceae;g__Pseudescherichia | Non-responder | -2.64 | 0.0077 |
| d__Bacteria;p__Proteobacteria;c__Gammaproteobacteria;o__Enterobacterales;f__Enterobacteriaceae;g__Yersinia;s__Yersinia mollaretii | Non-responder | -2.93 | 0.0104 |
| d__Bacteria;p__Campylobacterota;c__Campylobacteria;o__Campylobacterales;f__Campylobacteraceae;g__Campylobacter;s__Campylobacter fetus_A | Non-responder | -2.34 | 0.0107 |
| d__Bacteria;p__Firmicutes_I;c__Bacilli_A;o__Paenibacillales;f__Paenibacillaceae;g__Paenibacillus_F;s__Paenibacillus_F sp000411255 | Non-responder | -2.53 | 0.0157 |
| d__Bacteria;p__Firmicutes_I;c__Bacilli_A;o__Paenibacillales;f__Paenibacillaceae;g__Paenibacillus_F | Non-responder | -2.53 | 0.0157 |
| d__Bacteria;p__Firmicutes_A;c__Clostridia;o__Peptostreptococcales;f__Peptostreptococcaceae;g__Intestinibacter;s__Intestinibacter bartlettii | Non-responder | -2.08 | 0.0176 |
| d__Bacteria;p__Proteobacteria;c__Gammaproteobacteria;o__Enterobacterales;f__Enterobacteriaceae;g__Pseudescherichia;s__Pseudescherichia sp002298805 | Non-responder | -2.53 | 0.0176 |
| d__Bacteria;p__Firmicutes_A;c__Clostridia;o__Oscillospirales;f__Acutalibacteraceae;g__UBA1417;s__OTU_2066 | Non-responder | -4.23 | 0.0186 |
| d__Bacteria;p__Firmicutes_A;c__Clostridia;o__Oscillospirales;f__Oscillospiraceae;g__CAG-103 | Non-responder | -2.34 | 0.0208 |
| d__Bacteria;p__Fusobacteriota;c__Fusobacteriia;o__Fusobacteriales;f__Leptotrichiaceae;g__Leptotrichia;s__Leptotrichia wadei | Non-responder | -2.12 | 0.0203 |
| d__Bacteria;p__Proteobacteria;c__Gammaproteobacteria;o__Enterobacterales;f__Enterobacteriaceae;g__Pantoea;s__Pantoea vagans_A | Non-responder | -4.05 | 0.0225 |
| d__Bacteria;p__Firmicutes;c__Bacilli;o__Bacillales_A;f__Planococcaceae;g__Kurthia;s__Kurthia massiliensis | Non-responder | -2.45 | 0.0258 |
| d__Bacteria;p__Firmicutes_A;c__Clostridia;o__Oscillospirales;f__Oscillospiraceae;g__CAG-103;s__CAG-103 sp000432375 | Non-responder | -2.74 | 0.0272 |
| d__Bacteria;p__Firmicutes;c__Bacilli;o__Bacillales_A;f__Planococcaceae;g__Kurthia | Non-responder | -2.03 | 0.0287 |
| d__Bacteria;p__Verrucomicrobiota;c__Verrucomicrobiae;o__Verrucomicrobiales;f__Akkermansiaceae;g__Akkermansia;s__OTU_4717 | Non-responder | -5.59 | 0.0287 |
| d__Bacteria;p__Bacteroidota;c__Bacteroidia;o__Bacteroidales;f__Porphyromonadaceae;g__Porphyromonas;s__Porphyromonas somerae_A | Non-responder | -2.48 | 0.0287 |
| d__Bacteria;p__Firmicutes_A;c__Clostridia;o__Tissierellales;f__Ezakiellaceae;g__Ezakiella;s__Ezakiella massiliensis | Non-responder | -2.62 | 0.0302 |
| d__Bacteria;p__Firmicutes_A;c__Clostridia;o__Oscillospirales;f__Ruminococcaceae;g__Negativibacillus | Non-responder | -2.88 | 0.0318 |
| d__Bacteria;p__Firmicutes;c__Bacilli;o__Lactobacillales;f__Enterococcaceae;g__Enterococcus_B;s__Enterococcus_B faecium_B | Non-responder | -2.89 | 0.0353 |
| d__Bacteria;p__Bacteroidota;c__Bacteroidia;o__Bacteroidales;f__Bacteroidaceae;g__Bacteroides_A;s__OTU_4928 | Non-responder | -2.27 | 0.0411 |
| d__Bacteria;p__Firmicutes_A;c__Clostridia;o__4C28d-15;f__CAG-727;g__OTU_2912 | Non-responder | -2.63 | 0.0431 |
| d__Bacteria;p__Proteobacteria;c__Gammaproteobacteria;o__Enterobacterales;f__Enterobacteriaceae;g__Nissabacter;s__Nissabacter archeti | Non-responder | -2.55 | 0.0454 |
| d__Bacteria;p__Firmicutes_A;c__Clostridia;o__Peptostreptococcales;f__Peptostreptococcaceae;g__Intestinibacter;s__Intestinibacter bartlettii;t__OTU_596 | Non-responder | -2.84 | 0.0454 |
| d__Archaea;p__Thermoplasmatota;c__Thermoplasmata;o__Methanomassiliicoccales;f__Methanomethylophilaceae;g__UBA71;s__OTU_19 | Non-responder | -4.26 | 0.0476 |
| d__Bacteria;p__Proteobacteria;c__Gammaproteobacteria;o__Enterobacterales;f__Enterobacteriaceae;g__Morganella;s__Morganella morganii_A | Non-responder | -8.5 | 0.0476 |
| d__Bacteria;p__Proteobacteria;c__Gammaproteobacteria;o__Enterobacterales;f__Enterobacteriaceae;g__Nissabacter | Non-responder | -2.45 | 0.0476 |
| d__Bacteria;p__Proteobacteria;c__Gammaproteobacteria;o__Enterobacterales;f__Enterobacteriaceae;g__Yersinia;s__Yersinia kristensenii | Non-responder | -2.87 | 0.0476 |
| d__Bacteria;p__Firmicutes_A;c__Clostridia;o__Tissierellales;f__Helcococcaceae;g__Anaerococcus;s__Anaerococcus lactolyticus | Non-responder | -2.26 | 0.0476 |

FIG. 4D

| GTDB Taxonomy | NCBI Taxonomy |
|---|---|
| d__Bacteria; p__Firmicutes_A; c__Clostridia; o__TANB77; f__CAG-508; g__CAG-269; s__CAG-465 sp000431335 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-465; s__CAG-465 sp000433135 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-465; g__CAG-465; s__CAG-465 sp000433335 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-269; s__CAG-269 sp001916055 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-465; g__CAG-465; s__CAG-465 sp000433755 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-793; s__CAG-793 sp000433915 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-492; s__CAG-492 sp000434015 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-452; s__CAG-452 sp000434035 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-245; s__CAG-245 sp000434195 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-492; s__CAG-492 sp000434335 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-245; s__CAG-245 sp000435175 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-273; s__CAG-273 sp003507395 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-269; s__CAG-269 sp000435535 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-273; s__CAG-273 sp000435755 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-269; s__CAG-269 sp001916065 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-269; s__CAG-269 sp000437215 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-354; s__CAG-354 sp001915925 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-273; s__CAG-273 sp000437855 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-269; s__CAG-269 sp003525075 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-269; s__CAG-269 sp000438255 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-273; s__CAG-273 sp000438355 | d__Bacteria; p__Firmicutes; c__Clostridia; o__Clostridiales; f__Clostridiaceae; g__Clostridium; s__ |

FIG. 5A

| GTDB Taxonomy | NCBI Taxonomy |
|---|---|
| d__Bacteria; p__Firmicutes_A; c__Clostridia; o__TANB77; f__CAG-508; g__CAG-354; s__CAG-354 sp001915925 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-269; s__CAG-269 sp001915995 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-269; s__CAG-269 sp001916005 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-269; s__CAG-269 sp001916035 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-269; s__CAG-269 sp001916055 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-269; s__CAG-269 sp001916065 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-245; s__CAG-245 sp000435175 | d__Bacteria; p__Firmicutes; c__Clostridia; o__Clostridiales; f__; g__; s__ |
| d__Bacteria; p__Firmicutes_A; c__Clostridia; o__TANB77; f__UBA1234; g__UBA1234; s__UBA1234 sp002308995 | d__Bacteria; p__Firmicutes; c__Clostridia; o__Clostridiales; f__; g__; s__ |
| d__Bacteria; p__Firmicutes_A; c__Clostridia; o__TANB77; f__CAG-508; g__CAG-452; s__CAG-452 sp002314935 | d__Bacteria; p__Firmicutes; c__Clostridia; o__Clostridiales; f__; g__; s__ |
| d__Bacteria; p__Firmicutes_A; c__Clostridia; o__TANB77; f__CAG-508; g__CAG-269; s__CAG-269 sp002372935 | d__Bacteria; p__Firmicutes; c__Clostridia; o__Clostridiales; f__; g__; s__ |
| d__Bacteria; p__Firmicutes_A; c__Clostridia; o__TANB77; f__CAG-508; g__CAG-793; s__CAG-793 sp002393975 | d__Bacteria; p__Firmicutes; c__Clostridia; o__Clostridiales; f__; g__; s__ |
| d__Bacteria; p__Firmicutes_A; c__Clostridia; o__TANB77; f__UBA1234; g__UBA1234; s__UBA1234 sp002404755 | d__Bacteria; p__Firmicutes; c__Clostridia; o__Clostridiales; f__; g__; s__ |
| d__Bacteria; p__Firmicutes_A; c__Clostridia; o__TANB77; f__CAG-508; g__UBA7001; s__UBA7001 sp002449785 | d__Bacteria; p__Firmicutes; c__Clostridia; o__Clostridiales; f__; g__; s__ |
| d__Bacteria; p__Firmicutes_A; c__Clostridia; o__TANB77; f__CAG-508; g__CAG-492; s__CAG-492 sp002633185 | d__Bacteria; p__Firmicutes; c__Clostridia; o__Clostridiales; f__Lachnospiraceae; g__; s__ |
| d__Bacteria; p__Firmicutes_A; c__Clostridia; o__TANB77; f__CAG-508; g__CAG-245; s__CAG-245 sp000435175 | d__Bacteria; p__Firmicutes; c__Clostridia; o__Clostridiales; f__Clostridiaceae; g__Clostridium; s__ |
| d__Bacteria; p__Firmicutes_A; c__Clostridia; o__TANB77; f__CAG-508; g__CAG-273; s__CAG-273 sp003507395 | Undefined |
| d__Bacteria; p__Firmicutes_A; c__Clostridia; o__TANB77; f__CAG-508; g__CAG-269; s__CAG-269 sp003518755 | Undefined |
| d__Bacteria; p__Firmicutes_A; c__Clostridia; o__TANB77; f__CAG-508; g__CAG-269; s__CAG-269 sp003525075 | Undefined |
| d__Bacteria; p__Firmicutes_A; c__Clostridia; o__TANB77; f__CAG-508; g__CAG-273; s__CAG-273 sp003534295 | Undefined |
| d__Bacteria; p__Firmicutes_A; c__Clostridia; o__TANB77; f__CAG-508; g__CAG-269; s__CAG-269 sp000431335 | Undefined |

FIG. 5B

METHOD FOR PREDICTING AND IMPROVING TREATMENT RESPONSE TO INTESTINAL MICROBIOME-BASED CANCER IMMUNOTHERAPY AND METHOD FOR SCREENING FOR CANDIDATE PREBIOTICS

RELATED APPLICATIONS

This application is a national phase entry of PCT international phase patent application No. PCT/KR2021/008284, filed Jun. 30, 2021 in the name of INDUSTRY-ACADEMIC COOPERATION FOUNDATION, YONSEI UNIVERSITY [KR], which claims the benefit of priority of Korean Patent Application No. 10-2020-0082994, filed Jul. 6, 2020 in the name of INDUSTRY-ACADEMIC COOPERATION FOUNDATION, YONSEI UNIVERSITY [KR]. The entire contents of the above-referenced applications and of all priority documents referenced in the Application Data Sheet filed herewith are hereby incorporated by reference for all purposes.

TECHNICAL FIELD

The present invention relates to a method for predicting a treatment response to immune checkpoint inhibitor-based anticancer therapy based on human intestinal microbiome information, probiotics, and fecal microbiota transplantation compositions for improving a treatment response, and a method for screening candidate prebiotics.

BACKGROUND ART

A primary and effective method in the treatment of cancer is surgical resection. However, since it is not easy to remove residual tumors or metastatic foci with surgical resection alone, treatment methods such as chemotherapy and radiation therapy have been combined with surgical resection. Despite the development of these various therapies, it is difficult to expect effective cancer treatment by the above-mentioned therapy due to multiple metastases or biochemical recurrence shown after surgical resection.

On the other hand, as another strategy for the treatment of cancer, researchers have proposed a therapy that restores an immune response by targeted agents to directly treat cancer by essentially treating an immune system. Such cancer immunotherapy may be effective in treating cancer for patients by regulating the immune response by targeting a so-called immune checkpoint, which acts as an off-switch in T cells of the immune system.

Meanwhile, in the cancer immunotherapy, patients may be divided into a group that shows a treatment response to immunotherapy and a group that does not show the treatment response. That is, although for patients who respond to specific cancer immunotherapy, it is effective to treat cancer using a cancer immunotherapy drug, for non-responsive patients, it may be insignificant in a cancer treatment effect. Thus, other anticancer therapies may be required for non-responders.

For this reason, for the early treatment of cancer, the development of a new therapy and further the development of a system for predicting a new treatment response capable of predicting treatment responses to existing therapies have been continuously required.

The background art of the invention has been prepared to further facilitate understanding of the present invention. It should not be understood that the matters described in the background art of the invention exist as prior arts.

DISCLOSURE

Technical Problem

Among cancer immunotherapy, particularly, programmed cell death-1 (PD-1)/programmed cell death ligand-1 (PD-L1) signaling blockade may exhibit a therapeutic effect on various types of cancers. Accordingly, the present inventors of the present invention paid attention to an anti-PD-1 therapy based on PD-1/PD-L1 blockade.

Meanwhile, in predicting a treatment response to PD-1/PD-L1 blockade, tumor PD-L1 expression by immunohistochemistry (IHC) may be used as a predictive biomarker for PD-1/PD-L1 blockade.

However, in the PD-L1 expression in tumor cells, the accuracy of predicting the treatment response of a PD-1/PD-L1 blocker, that is, an anti-PD-1 therapeutic agent, is not high enough to determine drug efficacy. More specifically, PD-L1 expression-negative patients may respond to PD-1/PD-L1 blockade, and PD-L1 expression-positive patients may not respond to PD-1/PD-L1 blockade. Furthermore, some responsive patients without PD-L1 may have a similar duration of response to patients with positive PD-L1. Moreover, the PD-L1 expression is dynamic and may change temporally and spatially. Such a change in PD-L1 expression may be the adaptive immune resistance exerted by the tumor.

In order to overcome these limitations, the present inventors of the present invention intended to develop a new biomarker capable of increasing the accuracy of predicting a treatment response to anti-PD-1 treatment. As a result, the present inventors of the present invention found that there was a significant difference in the enrichment of a specific bacterial clade among intestinal microbiome of responders and non-responders to anti-PD-1 treatment.

More specifically, it was found that a TANB77 clade had high enrichment among intestinal microbiome in feces isolated from patients having a positive response to anti-PD-1 treatment.

In particular, it was found that the relative abundance of the order TANB77 or taxa belonging to the order TANB77 of patients with a positive response to anti-PD-1 treatment was about 5 times higher than the relative abundance of the TANB77 taxa of patients with a negative response to the anti-PD-1 treatment.

Accordingly, the present inventors of the present invention recognized that the enrichment of the TANB77 taxa in gut microbiota may be used as a biomarker for predicting the treatment response to the anti-PD-1 treatment.

Furthermore, the present inventors of the present invention further found microorganisms with high enrichment among the intestinal microbiome of each of responders and non-responders to the anti-PD-1 treatment, and recognized that the microorganisms may be used as a biomarker for predicting the treatment response to the anti-PD-1 treatment.

It was noted that the levels of microorganisms including TANB77 of the present invention had significant differences between responders and non-responders to anti-PD-1 treatment, at a baseline before administration of a PD-1/PD-L1 blocker.

As a result, the present inventors of the present invention were able to develop a new prediction method capable of predicting responders or non-responders at a baseline by analyzing the enrichment of each microorganism.

In particular, the present method may provide information that may be effective for early diagnosis, rather than a conventional method for predicting a response to anti-PD-1 treatment which had predicted responders and non-responders after primary treatment. Through this, the present inventors of the present invention could expect improvement in diagnostic ability of treatment response prediction based on a predictive model, further survival rate prediction.

Therefore, an object of the present invention is to provide a method for predicting a treatment response to cancer immunotherapy configured to evaluate, from feces isolated from a patient, the enrichment of each specific intestinal microorganism including TANB77 taxa and evaluate a treatment response of the patient to cancer immunotherapy based on the enrichment of each of these microorganisms.

Another object of the present invention is to provide a probiotics composition for improving a treatment response to anti-PD-1-based cancer immunotherapy including TANB77 taxa.

Yet another object of the present invention is to provide a fecal microbiota transplantation composition for improving a treatment response to anti-PD-1-based cancer immunotherapy including TANB77 taxa.

Still another object of the present invention is to provide a method for screening candidate prebiotics for improving a treatment response to anti-PD-1-based cancer immunotherapy.

The objects of the present invention are not limited to the aforementioned objects, and other objects, which are not mentioned above, will be apparent to those skilled in the art from the following description.

Technical Solution

One aspect of the present invention provides a method for predicting a treatment response to cancer immunotherapy.

The prediction method includes: evaluating, from feces isolated from a patient, the enrichment of the order TANB77 according to the Genome Taxonomy Database (GTDB) phylogenetic classification or taxa belonging to the order TANB77, or a strain according to GTDB phylogenetic classification of at least one of CAG-269 sp000431335 species, CAG-465 sp000433135 species, CAG-465 sp000433335 species, CAG-269 sp001916055 species, CAG-465 sp000433755 species, CAG-793 sp000433915 species, CAG-492 sp000434015 species, CAG-452 sp000434035 species, CAG-245 sp000434195 species, CAG-492 sp000434335 species, CAG-245 sp000435175 species, CAG-273 sp003507395 species, CAG-269 sp000435535 species, CAG-273 sp000435755 species, CAG-269 sp001916065 species, CAG-269 sp000437215 species, CAG-354 sp001915925 species, CAG-273 sp000437855 species, CAG-269 sp003525075 species, CAG-269 sp000438255 species, CAG-273 sp000438355 species, CAG-269 sp001915995 species, CAG-269 sp001916005 species, CAG-269 sp001916035 species, UBA1234 sp002308995 species, CAG-452 sp002314935 species, CAG-269 sp002372935 species, CAG-793 sp002393975 species, UBA1234 sp002404755 species, UBA7001 sp002449785 species, CAG-492 sp002633185 species, CAG-269 sp003518755 species, CAG-273 sp003534295 species, CAG-269 genus, CAG-492 genus, CAG-793 genus, CAG-452 genus, CAG-245 genus, CAG-273 genus, CAG-354 genus, UBA7001 genus, CAG-465 genus, UBA1234 genus, CAG-508 family, CAG-465 family, and UBA1234 family according to GTDB phylogenetic classification, and evaluating a treatment response of the patient to cancer immunotherapy based on the enrichment of the TANB77 taxa or at least one strain according to GTDB phylogenetic classification.

According to an exemplary embodiment of the present invention, the cancer immunotherapy may be anti-PD-1 treatment, and the feces may be feces isolated from the patient before the anti-PD-1 treatment is performed.

According to another exemplary embodiment of the present invention, the feces may include gut microbiota. At this time, the evaluating of the enrichment may include determining the relative abundance of the TANB77 taxa or the at least one strain according to GTDB phylogenetic classification in the gut microbiota, and the evaluating of the treatment response may include evaluating the patient as having a positive treatment response to the treatment of the cancer immunotherapy when the relative abundance is a predetermined level or higher.

According to yet another exemplary embodiment of the present invention, the predetermined level of the relative abundance of the TANB77 taxa may be 0.01% to 0.5%.

According to yet another exemplary embodiment of the present invention, the evaluating of the enrichment may further include evaluating, from the feces, the enrichment of the TANB77 taxa, and the enrichment of at least one additional strain of *Faecalicatena torques* species, CAG 269 genus, *Dethiosulfovibrio naceae* family, *Desulfovibrio piger* species, CAG-274 family, CAG-508 family, CAG-521 genus, *Mailhella* genus, UBA3700 family, CAG-273 sp000438355 species, *Risungbinella* genus, Thermoactinomycetaceae family, *Risungbinella massiliensis* species, and CAG-245 genus according to GTDB phylogenetic classification. At this time, the evaluating of a treatment response may further include evaluating a treatment response of the patient to cancer immunotherapy based on the enrichment of the TANB77 taxa and the enrichment of at least one additional strain.

According to yet another exemplary embodiment of the present invention, the evaluating of the treatment response may further include evaluating the patient as having a positive treatment response to the treatment of the cancer immunotherapy, when the enrichment of the TANB77 taxa and at least one additional strain is a predetermined level or higher.

According to yet another exemplary embodiment of the present invention, the prediction method may further include evaluating, from the feces, the enrichment of at least one additional strain of *Intestinibacter bartlettii* species, *Intestinibacter* genus, *Morganella morganii* species, CAG 103 sp000432375 species, *Negativibacillus* genus, CAG 83 sp000431575 species, CAG 103 genus, Rs-D84 genus, CAG-873 genus, *Collinsella* genus, *Butyricicoccus* genus, *Pseudescherichia* genus, *Yersinia mollaretii* species, *Campylobacter* fetus_A species, *Paenibacillus_F* sp000411255 species, *Paenibacillus_F* genus, *Pseudescherichia* sp002298805 species, UBA1417 genus, CAG-103 genus, *Leptotricia wadei* species, *Pantoea vagans_A* species, *Kurthia massiliensis* species, CAG-103 sp000432375 species, *Kurthia* genus, *Akkermansia* genus, *Porphyromonas somerae* A species, *Ezakiella massiliensis* species, *Enterococcus_B faecium_B* species, *Bacteroides* A genus, CAG-727 family, *Nissabacter archeti* species, UBA71 genus, *Morganella morganii* A species, *Nissabacter* genus, *Yersinia kristensenii* species, and *Anaerococcus lactolyticus* species according to GTDB phylogenetic classification, and evaluating a treatment response based on the enrichment of the at least one additional strain.

According to yet another exemplary embodiment of the present invention, the evaluating of the treatment response may include evaluating the patient as having a negative treatment response to the treatment of the cancer immunotherapy, when the enrichment of at least one additional strain is a predetermined level or higher.

According to yet another exemplary embodiment of the present invention, the patient may be a patient suspected of having at least one disease selected from the group consisting of non-small cell lung cancer, skin melanoma, head and neck cancer, stomach cancer, liver cancer, bone cancer, pancreatic cancer, skin cancer, uterine cancer, ovarian cancer, rectal cancer, colorectal cancer, colon cancer, breast cancer, uterine sarcoma, fallopian tube carcinoma, endometrial carcinoma, cervical carcinoma, vaginal carcinoma, vulvar carcinoma, esophageal cancer, laryngeal cancer, small intestine cancer, thyroid cancer, parathyroid cancer, sarcoma of the soft tissue, urethral cancer, penile cancer, prostate cancer, chronic or acute leukemia, childhood solid tumor, differentiated lymphoma, bladder cancer, kidney cancer, renal cell carcinoma, renal pelvic carcinoma, primary central nervous system lymphoma, spinal cord tumor, brainstem glioma, and pituitary adenoma.

Another aspect of the present invention provides a method for predicting a treatment response to cancer immunotherapy.

The prediction method includes evaluating, from feces isolated from a patient, the enrichment of a strain according to NCBI phylogenetic classification of at least one of phylogenetic classification IDs: 1262796, 1262847, 1262772, 1262800, 1262811, 1262840, 1262822, 1262810, 1262839, 1262813, 1262784, 1262841, 1262823, 1262815, 1262812, 1262807, 1262799, 1262820, 1262788, 1262801, 1262789, 1896989, 1896977, 1896978, 1896979, 1896980, 1896981, 1896986, 1950810, 1950830, 1950862, 1950880, 1950887, 1950920, 1958817, and 1506 according to National Center for Biotechnology Information (NCBI) phylogenetic classification, and predicting a treatment response of the patient to cancer immunotherapy based on the enrichment of the at least one strain according to NCBI phylogenetic classification.

According to an exemplary embodiment of the present invention, the prediction method may further include evaluating, from the feces, the enrichment of the strain according to NCBI phylogenetic classification, and the enrichment of at least one additional strain of *Faecalicatena torques* species, CAG 269 genus, *Dethiosulfovibrio naceae* family, *Desulfovibrio piger* species, CAG-274 family, CAG-508 family, CAG-521 genus, *Mailhella* genus, UBA3700 family, CAG-273 sp000438355 species, *Risungbinella* genus, Thermoactinomycetaceae family, *Risungbinella massiliensis* species, and CAG-245 genus according to GTDB phylogenetic classification, and predicting a treatment response of the patient to cancer immunotherapy based on the enrichment of the strain according to NCBI phylogenetic classification and the enrichment of the at least one additional strain.

According to yet another exemplary embodiment of the present invention, the prediction method may further include evaluating, from the feces, the enrichment of at least one additional strain of *Intestinibacter bartlettii* species, *Intestinibacter* genus, *Morganella morganii* species, CAG 103 sp000432375 species, *Negativibacillus* genus, CAG 83 sp000431575 species, CAG 103 genus, Rs-D84 genus, CAG-873 genus, *Collinsella* genus, *Butyricicoccus* genus, *Pseudescherichia* genus, *Yersinia mollaretii* species, *Campylobacter* fetus_A species, *Paenibacillus_F* sp000411255 species, *Paenibacillus_F* genus, *Pseudescherichia* sp002298805 species, UBA1417 genus, CAG-103 genus, *Leptotricia wadei* species, *Pantoea vagans_A* species, *Kurthia massiliensis* species, CAG-103 sp000432375 species, *Kurthia* genus, *Akkermansia* genus, *Porphyromonas somerae* A species, *Ezakiella massiliensis* species, *Enterococcus_B faecium_B* species, *Bacteroides* A genus, CAG-727 family, *Nissabacter archeti* species, UBA71 genus, *Morganella morganii* A species, *Nissabacter* genus, *Yersinia kristensenii* species, and *Anaerococcus lactolyticus* species according to GTDB phylogenetic classification, and predicting a treatment response based on the enrichment of the at least one additional strain.

Yet another aspect of the present invention provides a probiotics composition including the order TANB77 according to GTDB phylogenetic classification or taxa belonging to the order TANB77, or at least one strain of CAG-269 sp000431335 species, CAG-465 sp000433135 species, CAG-465 sp000433335 species, CAG-269 sp001916055 species, CAG-465 sp000433755 species, CAG-793 sp000433915 species, CAG-492 sp000434015 species, CAG-452 sp000434035 species, CAG-245 sp000434195 species, CAG-492 sp000434335 species, CAG-245 sp000435175 species, CAG-273 sp003507395 species, CAG-269 sp000435535 species, CAG-273 sp000435755 species, CAG-269 sp001916065 species, CAG-269 sp000437215 species, CAG-354 sp001915925 species, CAG-273 sp000437855 species, CAG-269 sp003525075 species, CAG-269 sp000438255 species, CAG-273 sp000438355 species, CAG-269 sp001915995 species, CAG-269 sp001916005 species, CAG-269 sp001916035 species, UBA1234 sp002308995 species, CAG-452 sp002314935 species, CAG-269 sp002372935 species, CAG-793 sp002393975 species, UBA1234 sp002404755 species, UBA7001 sp002449785 species, CAG-492 sp002633185 species, CAG-269 sp003518755 species, CAG-273 sp003534295 species, CAG-269 genus, CAG-492 genus, CAG-793 genus, CAG-452 genus, CAG-245 genus, CAG-273 genus, CAG-354 genus, UBA7001 genus, CAG-465 genus, UBA1234 genus, CAG-508 family, CAG-465 family, and UBA1234 family according to GTDB phylogenetic classification.

Still another aspect of the present invention provides a fecal microbiota transplantation composition as a composition for cancer immunotherapy including the order TANB77 according to GTDB phylogenetic classification or taxa belonging to the order TANB77, or at least one strain of CAG-269 sp000431335 species, CAG-465 sp000433135 species, CAG-465 sp000433335 species, CAG-269 sp001916055 species, CAG-465 sp000433755 species, CAG-793 sp000433915 species, CAG-492 sp000434015 species, CAG-452 sp000434035 species, CAG-245 sp000434195 species, CAG-492 sp000434335 species, CAG-245 sp000435175 species, CAG-273 sp003507395 species, CAG-269 sp000435535 species, CAG-273 sp000435755 species, CAG-269 sp001916065 species, CAG-269 sp000437215 species, CAG-354 sp001915925 species, CAG-273 sp000437855 species, CAG-269 sp003525075 species, CAG-269 sp000438255 species, CAG-273 sp000438355 species, CAG-269 sp001915995 species, CAG-269 sp001916005 species, CAG-269 sp001916035 species, UBA1234 sp002308995 species, CAG-452 sp002314935 species, CAG-269 sp002372935 species, CAG-793 sp002393975 species, UBA1234 sp002404755 species, UBA7001 sp002449785 species, CAG-492 sp002633185 species, CAG-269 sp003518755 species, CAG-273 sp003534295 species, CAG-269 genus, CAG-492 genus, CAG-793 genus, CAG-452 genus, CAG-245 genus, CAG-273 genus, CAG-354 genus, UBA7001 genus, CAG-465 genus, UBA1234 genus, CAG-508 family, CAG-465 family, and UBA1234 family according to GTDB phylogenetic classification.

Still yet another aspect of the present invention provides a method for screening candidate prebiotics.

The screening method includes evaluating, from feces isolated from a patient, the enrichment of the order TANB77 according to GTDB phylogenetic classification or taxa belonging to the order TANB77, or at least one strain of CAG-269 sp000431335 species, CAG-465 sp000433135 species, CAG-465 sp000433335 species, CAG-269 sp001916055 species, CAG-465 sp000433755 species, CAG-793 sp000433915 species, CAG-492 sp000434015 species, CAG-452 sp000434035 species, CAG-245 sp000434195 species, CAG-492 sp000434335 species, CAG-245 sp000435175 species, CAG-273 sp003507395 species, CAG-269 sp000435535 species, CAG-273 sp000435755 species, CAG-269 sp001916065 species, CAG-269 sp000437215 species, CAG-354 sp001915925 species, CAG-273 sp000437855 species, CAG-269 sp003525075 species, CAG-269 sp000438255 species, CAG-273 sp000438355 species, CAG-269 sp001915995 species, CAG-269 sp001916005 species, CAG-269 sp001916035 species, UBA1234 sp002308995 species, CAG-452 sp002314935 species, CAG-269 sp002372935 species, CAG-793 sp002393975 species, UBA1234 sp002404755 species, UBA7001 sp002449785 species, CAG-492 sp002633185 species, CAG-269 sp003518755 species, CAG-273 sp003534295 species, CAG-269 genus, CAG-492 genus, CAG-793 genus, CAG-452 genus, CAG-245 genus, CAG-273 genus, CAG-354 genus, UBA7001 genus, CAG-465 genus, UBA1234 genus, CAG-508 family, CAG-465 family, and UBA1234 family according to GTDB phylogenetic classification, before administering candidate prebiotics, re-evaluating, from the feces isolated from the patient, the enrichment of the TANB77 taxa or the at least one strain, after administering the candidate prebiotics, and evaluating the candidate prebiotics by comparing the enrichment of the TANB77 taxa or the at least one strain before administering the candidate prebiotics with the enrichment of the TANB77 taxa after administering the candidate prebiotics.

According to an exemplary embodiment of the present invention, the candidate prebiotics may be candidate prebiotics for enhancement of the enrichment of the order TANB77 according to GTDB phylogenetic classification or taxa belonging to the order TANB77, or at least one strain of CAG-269 sp000431335 species, CAG-465 sp000433135 species, CAG-465 sp000433335 species, CAG-269 sp001916055 species, CAG-465 sp000433755 species, CAG-793 sp000433915 species, CAG-492 sp000434015 species, CAG-452 sp000434035 species, CAG-245 sp000434195 species, CAG-492 sp000434335 species, CAG-245 sp000435175 species, CAG-273 sp003507395 species, CAG-269 sp000435535 species, CAG-273 sp000435755 species, CAG-269 sp001916065 species, CAG-269 sp000437215 species, CAG-354 sp001915925 species, CAG-273 sp000437855 species, CAG-269 sp003525075 species, CAG-269 sp000438255 species, CAG-273 sp000438355 species, CAG-269 sp001915995 species, CAG-269 sp001916005 species, CAG-269 sp001916035 species, UBA1234 sp002308995 species, CAG-452 sp002314935 species, CAG-269 sp002372935 species, CAG-793 sp002393975 species, UBA1234 sp002404755 species, UBA7001 sp002449785 species, CAG-492 sp002633185 species, CAG-269 sp003518755 species, CAG-273 sp003534295 species, CAG-269 genus, CAG-492 genus, CAG-793 genus, CAG-452 genus, CAG-245 genus, CAG-273 genus, CAG-354 genus, UBA7001 genus, CAG-465 genus, UBA1234 genus, CAG-508 family, CAG-465 family, and UBA1234 family according to GTDB phylogenetic classification, and the feces may be feces isolated from the patient before and after the candidate prebiotics are administered.

Hereinafter, the present invention will be described in more detail with reference to Examples. However, these Examples are only illustrative of the present invention, and the scope of the present invention is not limited to these Examples.

Advantageous Effects

According to the present invention, it is possible to provide a new system for predicting a treatment response capable of predicting a treatment response to cancer immunotherapy, particularly PD-1/PD-L1 blockade.

More specifically, according to the present invention, it is possible to provide a biomarker with high accuracy of prediction for a treatment response with respect to feces obtained from a patient before anti-PD-1 treatment is performed.

Accordingly, according to the present invention, it is possible to provide information that may be effective for early diagnosis, rather than a conventional method for predicting a response to anti-PD-1 treatment based on biomarkers, which had predicted responders and non-responders after primary treatment.

In addition, according to the present invention, it is possible to easily select an effective treatment according to whether a treatment response to the patient is positive or negative by accurately and rapidly providing the response to the anti-PD-1 treatment.

According to the present invention, it is possible to provide information to predict a treatment response for patients suspected of having various cancers to which anti-PD-1 treatment may be applied. For example, according to the present invention, it is possible to provide information on a treatment response to anti-PD-1 treatment for patients suspected of having non-small cell lung cancer, skin melanoma, head and neck cancer, stomach cancer, liver cancer, bone cancer, pancreatic cancer, skin cancer, uterine cancer, ovarian cancer, rectal cancer, colorectal cancer, colon cancer, breast cancer, uterine sarcoma, fallopian tube carcinoma, endometrial carcinoma, cervical carcinoma, vaginal carcinoma, vulvar carcinoma, esophageal cancer, laryngeal cancer, small intestine cancer, thyroid cancer, parathyroid cancer, sarcoma of the soft tissue, urethral cancer, penile cancer, prostate cancer, chronic or acute leukemia, childhood solid tumor, differentiated lymphoma, bladder cancer, kidney cancer, renal cell carcinoma, renal pelvic carcinoma, primary central nervous system lymphoma, spinal cord tumor, brainstem glioma, or pituitary adenoma.

The effects of the present invention are not limited by the foregoing, and other various effects are anticipated herein.

DESCRIPTION OF DRAWINGS

FIG. 4A lists microorganisms with relatively high enrichment among the intestinal microbiome of responders to anti-PD-1 treatment based on the Genome Taxonomy Database taxonomy (GTDB).

FIG. 4B lists microorganisms with relatively high enrichment among the intestinal microbiome of non-responders to anti-PD-1 treatment based on the GTDB.

FIG. 4C lists microorganisms with relatively high enrichment among the intestinal microbiome of responders to anti-PD-1 treatment based on a Mann-Whitney U test.

FIG. 4D lists microorganisms with relatively high enrichment among the intestinal microbiome of non-responders to anti-PD-1 treatment based on the Mann-Whitney U test.

FIGS. 5A and 5B illustrate results of phylogenetic classification based on GTDB and NCBI for a TANB77 strain used in various exemplary embodiments of the present invention.

MODES OF THE INVENTION

Figure 1:
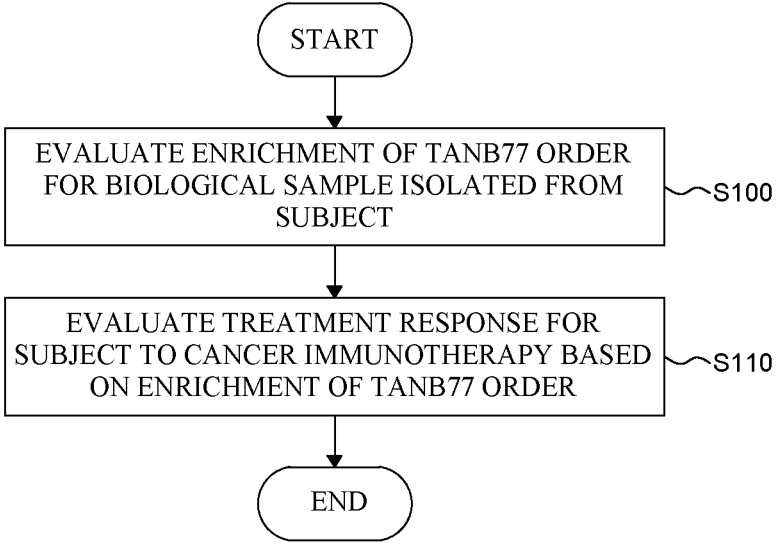
FIG. 1 exemplarily illustrates a procedure of a method for predicting a treatment response to cancer immunotherapy according to an exemplary embodiment of the present invention.

Advantages and features of the present invention, and methods for accomplishing the same will be more clearly understood from exemplary embodiments to be described below in detail with reference to the accompanying drawings. However, the present invention is not limited to the exemplary embodiments set forth below, and will be embodied in various different forms. The exemplary embodiments are just for rendering the disclosure of the present invention complete and are set forth to provide a complete understanding of the scope of the invention to a person with ordinary skill in the art to which the present invention pertains, and the present invention will only be defined by the scope of the claims.

Hereinafter, terms used within the present specification will be described for clarity of explanation.

As used herein, the term "cancer immunotherapy" refers to anticancer therapy using a cancer immunotherapy agent that enhances the specificity, memory, and adaptiveness of the immune system. At this time, the cancer immunotherapy has fewer side effects by using the immune system of the human body to attack only cancer cells accurately and may provide a continuous anticancer effect for patients who are effective with immune anticancer drugs by using the memory and adaptiveness of the immune system.

According to the feature of the present invention, the cancer immunotherapy may be anti-PD-1 treatment. In this case, the anti-PD-1 therapy may be applied as anticancer therapy for patients with various types of cancers.

As used herein, the term "anti-PD-1 treatment" may be a therapy configured to block a mechanism in which T cells do not attack tumor cells. More specifically, the anti-PD-1 treatment may be based on blocking the binding of PD-L1 and PD-L2 as immune checkpoint ligands of a surface protein of tumor cells and PD-1 as an immune checkpoint receptor of a protein on the surface of T cells. For example, when the cancer immunotherapy drug binds to a PD-1 receptor of the T cells, the cancer immunotherapy drug may suppress an evasion function of the T cells to tumor cells. Accordingly, in the present specification, the "anti-PD-1 treatment" may be used in the same meaning as "PD-1/PD-L1 blockade".

As used herein, the term "patient" may be a subject to evaluate a treatment response to cancer immunotherapy, more preferably, anti-PD-1 treatment.

For example, the patient may be patients with non-small cell lung cancer, skin melanoma, head and neck cancer, stomach cancer, liver cancer, bone cancer, pancreatic cancer, skin cancer, uterine cancer, ovarian cancer, rectal cancer, colorectal cancer, colon cancer, breast cancer, uterine sarcoma, fallopian tube carcinoma, endometrial carcinoma, cervical carcinoma, vaginal carcinoma, vulvar carcinoma, esophageal cancer, laryngeal cancer, small intestine cancer, thyroid cancer, parathyroid cancer, sarcoma of the soft tissue, urethral cancer, penile cancer, prostate cancer, chronic or acute leukemia, childhood solid tumor, differentiated lymphoma, bladder cancer, kidney cancer, renal cell carcinoma, renal pelvic carcinoma, primary central nervous system lymphoma, spinal cord tumor, brainstem glioma, or pituitary adenoma. Preferably, the patient whose response to the anti-PD-1 treatment of the present invention is to be predicted may be a patient with non-small cell lung cancer, melanoma, and kidney cancer. However, the patients may be various individuals with cancer that are responsive to anti-PD-1 therapy, but is not limited thereto.

As used herein, the term "treatment response" may mean evaluating whether there is a response in which binding between the receptor of the surface of the T cell and the ligand of the surface of the tumor cell is blocked by an immune checkpoint blocker such as a PD-1/PD-L1 blocker.

Meanwhile, the term "positive treatment response" as used herein may refer to partial remission in which the size of the tumor is reduced by 30% or more after treatment with the PD-1/PD-L1 blocker, or a stable state in which the size of the tumor is not increased by 20% or more. However, the present invention is not limited thereto, and the positive treatment response may include the occurrence of any response associated with symptom relief or favorable prognosis by the immune checkpoint blocker. Accordingly, in patients with a positive anti-PD-1 treatment response, symptoms associated with the above-mentioned cancers may be alleviated by anti-PD-1 treatment, and patients with a negative anti-PD-1 treatment response may be relatively poor in the prognosis according to anti-PD-1 treatment.

Meanwhile, in the present specification, the patients with the positive anti-PD-1 treatment response may be used the same as responders or responders to anti-PD-1 treatment. Furthermore, meanwhile, in the present specification, the patients with the negative anti-PD-1 treatment response may be used the same as non-responders or non-responders to anti-PD-1 treatment.

The term "feces" as used herein may be feces obtained from a patient before or after the anti-PD-1 treatment is performed, but are not limited thereto.

The term "TANB77 taxa" as used herein may refer to the order TANB77 or taxa belonging to the order TANB77, and may refer to strains of a TANB77 clade.

The TANB77 taxa may include a strain according to GTDB phylogenetic classification of at least one of CAG-269 sp000431335 species, CAG-465 sp000433135 species, CAG-465 sp000433335 species, CAG-269 sp001916055 species, CAG-465 sp000433755 species, CAG-793 sp000433915 species, CAG-492 sp000434015 species, CAG-452 sp000434035 species, CAG-245 sp000434195 species, CAG-492 sp000434335 species, CAG-245 sp000435175 species, CAG-273 sp003507395 species, CAG-269 sp000435535 species, CAG-273 sp000435755 species, CAG-269 sp001916065 species, CAG-269 sp000437215 species, CAG-354 sp001915925 species, CAG-273 sp000437855 species, CAG-269 sp003525075 species, CAG-269 sp000438255 species, CAG-273 sp000438355 species, CAG-269 sp001915995 species, CAG-269 sp001916005 species, CAG-269 sp001916035 species, UBA1234 sp002308995 species, CAG-452 sp002314935 species, CAG-269 sp002372935 species, CAG-793 sp002393975 species, UBA1234 sp002404755 species, UBA7001 sp002449785 species, CAG-492 sp002633185 species, CAG-269 sp003518755 species, CAG-273 sp003534295 species, CAG-269 genus, CAG-492 genus, CAG-793 genus, CAG-452 genus, CAG-245 genus, CAG-273 genus, CAG-354 genus, UBA7001 genus, CAG-465 genus, UBA1234 genus, CAG-508 family, CAG-465 family, and UBA1234 family according to GTDB phylogenetic classification.

However, the present invention is not limited thereto, and the TANB77 taxa may include a strain according to NCBI phylogenetic classification of at least one of phylogenetic classification IDs: 1262796, 1262847, 1262772, 1262800, 1262811, 1262840, 1262822, 1262810, 1262839, 1262813, 1262784, 1262841, 1262823, 1262815, 1262812, 1262807, 1262799, 1262820, 1262788, 1262801, 1262789, 1896989, 1896977, 1896978, 1896979, 1896980, 1896981, 1896986, 1950810, 1950830, 1950862, 1950880, 1950887, 1950920, 1958817, and 1506 according to NCBI phylogenetic classification.

At this time, the TANB77 taxa may have high enrichment in the gut microbiota of responders responding to anti-PD-1 treatment. More specifically, the relative abundance of the TANB77 taxa in the gut microbiota of patients with a positive anti-PD-1 treatment response may be about 3 to 5 times higher than that of patients with a negative anti-PD-1 treatment response. Accordingly, the enrichment of a TANB77 strain in the gut microbiota may be used as a biomarker for predicting a treatment response to cancer immunotherapy, particularly anti-PD-1 treatment.

Meanwhile, based on the GTDB classification, the TANB77 strain is a strain phylogenetically distinguished from the Clostridium genus, or Clostridiales or Clostridia class, and a TANB77 genome was also assembled into a genome independent of genomes of strains of Clostridium genus, or Clostridiales or Clostridia class even in chicken and mouse intestinal metagenomes. More specifically, the TANB77 strain has a remarkably small-sized genome compared to that of the Clostridium genus.

The term "enrichment" as used herein may mean the degree of presence of a strain. Meanwhile, the enrichment may mean a relative abundance, particularly enrichment of a relative abundance of a specific strain associated with prediction of a treatment response to cancer immunotherapy such as TANB77 taxa in the gut microbiota. However, the present invention is not limited thereto.

As used herein, the term "predetermined level" may refer to a threshold for determining a negative or positive treatment response to cancer immunotherapy, particularly anti-PD-1 treatment.

More specifically, for prediction of the treatment response to the anti-PD-1 treatment, a predetermined level of the relative abundance of the TANB77 taxa in the gut microbiota may be 0.01% and 0.5%. Preferably, the predetermined level may be 0.05% to 0.2%. More preferably, the predetermined level may be 0.1% to 0.15%, but is not limited thereto.

For example, when the relative abundance of the TANB77 taxa in the gut microbiota of the patient is 0.12% or more before the anti-PD-1 treatment is performed, the patient may be predicted as having a positive treatment response to anti-PD-1 treatment, and in the case of less than 0.12%, the patient may be predicted as having a negative treatment response to anti-PD-1 treatment.

Meanwhile, in various exemplary embodiments of the present invention, for predicting the treatment response to cancer immunotherapy, particularly anti-PD-1, in addition to the enrichment of the TANB77 taxa, the enrichment of at least one strain of Faecalicatena torques species, CAG 269 genus, Dethiosulfovibrio naceae family, Desulfovibrio piger species, CAG-274 family, CAG-508 family, CAG-521 genus, Mailhella genus, UBA3700 family, CAG-273 sp000438355 species, Risungbinella genus, Thermoactinomycetaceae family, Risungbinella massiliensis species, and CAG-245 genus according to the GTDB phylogenetic classification, that is, the relative abundance in the gut microbiota may be evaluated.

For example, when the enrichment of the TANB77 taxa and the enrichment of at least one strain described above are the predetermined level or higher, the patient may be evaluated as having a positive treatment response to anti-PD-1 treatment.

In addition, for predicting the treatment response to anti-PD-1, the enrichment of at least one strain of Intestinibacter bartlettii species, Intestinibacter genus, Morganella morganii species, CAG 103 sp000432375 species, Negativibacillus genus, CAG 83 sp000431575 species, CAG 103 genus, Rs-D84 genus, CAG-873 genus, Collinsella genus, Butyricicoccus genus, Pseudescherichia genus, Yersinia mollaretii species, Campylobacter fetus_A species, Paenibacillus_F sp000411255 species, Paenibacillus_F genus, Pseudescherichia sp002298805 species, UBA1417 genus, CAG-103 genus, Leptotricia wadei species, Pantoea vagans_A species, Kurthia massiliensis species, CAG-103 sp000432375 species, Kurthia genus, Akkermansia genus, Porphyromonas somerae_A species, Ezakiella massiliensis species, Enterococcus_B faecium_B species, Bacteroides A genus, CAG-727 family, Nissabacter archeti species, UBA71 genus, Morganella morganii A species, Nissabacter genus, Yersinia kristensenii species, and Anaerococcus lactolyticus species according to GTDB phylogenetic classification, that is, the relative abundance in the gut microbiota may be evaluated.

For example, when the enrichment of at least one strain described above is the predetermined level or higher, the patient may be evaluated as having a negative treatment response to anti-PD-1 treatment.

As used herein, the term "screening" may mean screening of prebiotics.

More specifically, the screening may mean screening of prebiotics capable of increasing the enrichment of the intestinal TANB77 strain.

At this time, the "candidate prebiotics" may include a substance that may be expected to enhance cancer immunotherapy, particularly a PD-1/PD-L1 blocking effect by increasing the enrichment of the intestinal TANB77 strain.

Such the candidate prebiotics may also provide an improvement effect on symptoms according to at least one disease of non-small cell lung cancer, skin melanoma, head and neck cancer, stomach cancer, liver cancer, bone cancer, pancreatic cancer, skin cancer, uterine cancer, ovarian cancer, rectal cancer, colorectal cancer, colon cancer, breast cancer, uterine sarcoma, fallopian tube carcinoma, endometrial carcinoma, cervical carcinoma, vaginal carcinoma, vulvar carcinoma, esophageal cancer, laryngeal cancer, small intestine cancer, thyroid cancer, parathyroid cancer, sarcoma of the soft tissue, urethral cancer, penile cancer, prostate cancer, chronic or acute leukemia, childhood solid tumor, differentiated lymphoma, bladder cancer, kidney cancer, renal cell carcinoma, renal pelvic carcinoma, primary central nervous system lymphoma, spinal cord tumor, brainstem glioma, and pituitary adenoma, according to the enhancement of the PD-1/PD-L1 blocking effect.

For example, the candidate prebiotics capable of enhancing the enrichment of the intestinal TANB77 may be evaluated by evaluating the enrichment of the TANB77 taxa from the feces isolated from the patient before administration of the candidate prebiotics, re-evaluating the enrichment of the TANB77 taxa from the feces isolated from the patient after administration of the candidate prebiotics, and then comparing the enrichment of the TANB77 taxa before and after the administration.

At this time, when the relative abundance of the TANB77 taxa after administration of the candidate prebiotics is higher than that before the administration, the candidate prebiotics are effective in enhancing the enrichment of the TANB77 taxa and may also be determined as an adjuvant for PD-1/PD-L1 blockade.

As used herein, the term "fecal microbiota transplantation" may refer to transplanting microorganisms present in feces of a healthy individual into the intestine of a diseased individual.

In this case, the TANB77 taxa may also be provided as a fecal microbiota transplantation composition for cancer immunotherapy.

Hereinafter, a procedure of a method for predicting a treatment response to cancer immunotherapy according to an exemplary embodiment of the present invention will be described in detail with reference to FIG. 1.

FIG. 1 exemplarily illustrates a procedure of a method for predicting a treatment response to cancer immunotherapy according to an exemplary embodiment of the present invention.

Referring to FIG. 1, the method for predicting the treatment response to cancer immunotherapy according to an exemplary embodiment of the present invention is configured by evaluating, from feces isolated from a patient, the enrichment of the order TANB77 (S100), and predicting a treatment response of the patient to cancer immunotherapy on the basis of the enrichment of TANB77 taxa (S110).

According to the feature of the present invention, in the step of evaluating the enrichment (S110), in the feces isolated from the patient before the anti-PD-1 treatment is performed, the enrichment may be evaluated for the order TANB77 according to GTDB phylogenetic classification or taxa belonging to the order TANB77, or a strain according to GTDB phylogenetic classification of at least one of CAG-269 sp000431335 species, CAG-465 sp000433135 species, CAG-465 sp000433335 species, CAG-269 sp001916055 species, CAG-465 sp000433755 species, CAG-793 sp000433915 species, CAG-492 sp000434015 species, CAG-452 sp000434035 species, CAG-245 sp000434195 species, CAG-492 sp000434335 species, CAG-245 sp000435175 species, CAG-273 sp003507395 species, CAG-269 sp000435535 species, CAG-273 sp000435755 species, CAG-269 sp001916065 species, CAG-269 sp000437215 species, CAG-354 sp001915925 species, CAG-273 sp000437855 species, CAG-269 sp003525075 species, CAG-269 sp000438255 species, CAG-273 sp000438355 species, CAG-269 sp001915995 species, CAG-269 sp001916005 species, CAG-269 sp001916035 species, UBA1234 sp002308995 species, CAG-452 sp002314935 species, CAG-269 sp002372935 species, CAG-793 sp002393975 species, UBA1234 sp002404755 species, UBA7001 sp002449785 species, CAG-492 sp002633185 species, CAG-269 sp003518755 species, CAG-273 sp003534295 species, CAG-269 genus, CAG-492 genus, CAG-793 genus, CAG-452 genus, CAG-245 genus, CAG-273 genus, CAG-354 genus, UBA7001 genus, CAG-465 genus, UBA1234 genus, CAG-508 family, CAG-465 family, and UBA1234 family according to GTDB phylogenetic classification, or a strain according to NCBI phylogenetic classification of at least one of Taxonomy IDs: 1262796, 1262847, 1262772, 1262800, 1262811, 1262840, 1262822, 1262810, 1262839, 1262813, 1262784, 1262841, 1262823, 1262815, 1262812, 1262807, 1262799, 1262820, 1262788, 1262801, 1262789, 1896989, 1896977, 1896978, 1896979, 1896980, 1896981, 1896986, 1950810, 1950830, 1950862, 1950880, 1950887, 1950920, 1958817, and 1506 according to NCBI Taxonomy ID.

At this time, the patient may be a patient suspected of having at least one disease selected from the group consisting of non-small cell lung cancer, skin melanoma, head and neck cancer, stomach cancer, liver cancer, bone cancer, pancreatic cancer, skin cancer, uterine cancer, ovarian cancer, rectal cancer, colorectal cancer, colon cancer, breast cancer, uterine sarcoma, fallopian tube carcinoma, endometrial carcinoma, cervical carcinoma, vaginal carcinoma, vulvar carcinoma, esophageal cancer, laryngeal cancer, small intestine cancer, thyroid cancer, parathyroid cancer, sarcoma of the soft tissue, urethral cancer, penile cancer, prostate cancer, chronic or acute leukemia, childhood solid tumor, differentiated lymphoma, bladder cancer, kidney cancer, renal cell carcinoma, renal pelvic carcinoma, primary central nervous system lymphoma, spinal cord tumor, brainstem glioma, and pituitary adenoma.

According to another feature of the present invention, in the step of evaluating the enrichment (S100), in feces including the gut microbiota, the relative abundance of TANB77 taxa in the gut microbiota may be determined.

At this time, a predetermined level for the relative abundance of the TANB77 taxa may be 0.01% to 0.5%. Preferably, the predetermined level may be 0.05% to 0.2%. More preferably, the predetermined level may be 0.1% to 0.15%, but is not limited thereto.

According to yet another feature of the present invention, in the step of evaluating the enrichment (S100), with respect to the feces, the enrichment of the TANB77 taxa, and the enrichment of at least one strain of *Faecalicatena torques* species, CAG 269 genus, *Dethiosulfovibrio naceae* family, *Desulfovibrio piger* species, CAG-274 family, CAG-508 family, CAG-521 genus, *Mailhella* genus, UBA3700 family, CAG-273 sp000438355 species, *Risungbinella* genus, Thermoactinomycetaceae family, *Risungbinella massiliensis* species, and CAG-245 genus according to GTDB phylogenetic classification may be evaluated.

Next, in the step of predicting the treatment response (S110), on the basis of the enrichment of the TANB77 taxa, the treatment response of the patient to cancer immunotherapy, particularly anti-PD-1 treatment may be predicted.

According to the feature of the present invention, in the step of predicting the treatment response (S110), when the relative abundance of the TANB77 taxa in the gut microbiota is a predetermined level or higher, the patient may be predicted as having a positive treatment response to the treatment of cancer immunotherapy.

For example, in the step of evaluating the treatment response (S110), when the relative abundance of the TANB77 taxa in the gut microbiota of the patient is 0.12% or more before the anti-PD-1 treatment is performed, the patient may be evaluated as having a positive treatment response to anti-PD-1 treatment, and in the case of less than 0.12%, the patient may be evaluated as having a negative treatment response to anti-PD-1 treatment.

According to another feature of the present invention, in the step of evaluating the treatment response (S110), on the basis of the enrichment of the TANB77 taxa, and the enrichment of at least one positive factor microorganism of *Faecalicatena torques* species, CAG 269 genus, *Dethiosulfovibrio naceae* family, *Desulfovibrio piger* species, CAG-274 family, CAG-508 family, CAG-521 genus, *Mailhella* genus, UBA3700 family, CAG-273 sp000438355 species, *Risungbinella* genus, Thermoactinomycetaceae family, *Risungbinella massiliensis* species, and CAG-245 genus according to GTDB phylogenetic classification, the treatment response to the cancer immunotherapy may be predicted.

For example, in the step of predicting the treatment response (S110), when the enrichment of the TANB77 taxa and the enrichment of at least one positive factor microorganism described above are the predetermined level or higher, the patient may be predicted as having a positive treatment response to anti-PD-1 treatment.

Meanwhile, the prediction method according to various exemplary embodiments of the present invention is not limited to predicting the positive treatment response to anti-PD-1 treatment using the above-described microbial species.

For example, according to yet another feature of the present invention, with respect to the feces, there may be further performed evaluating the enrichment of at least one strain of *Intestinibacter bartlettii* species, *Intestinibacter* genus, *Morganella morganii* species, CAG 103 sp000432375 species, *Negativibacillus* genus, CAG 83 sp000431575 species, CAG 103 genus, Rs-D84 genus, CAG-873 genus, *Collinsella* genus, *Butyricicoccus* genus, *Pseudescherichia* genus, *Yersinia mollaretii* species, *Campylobacter* fetus_A A species, *Paenibacillus_F* sp000411255 species, *Paenibacillus_F* genus, *Pseudescherichia* sp002298805 species, UBA1417 genus, CAG-103 genus, *Leptotricia wadei* species, *Pantoea vagans_A* species, *Kurthia massiliensis* species, CAG-103 sp000432375 species, *Kurthia* genus, *Akkermansia* genus, *Porphyromonas somerae_A* species, *Ezakiella massiliensis* species, *Enterococcus_B faecium_B* species, *Bacteroides* A genus, CAG-727 family, *Nissabacter archeti* species, UBA71 genus, *Morganella morganii* A species, *Nissabacter* genus, *Yersinia kristensenii* species, and *Anaerococcus lactolyticus* species according to GTDB phylogenetic classification, and evaluating a treatment response on the basis of the enrichment of at least one negative factor microorganism.

For example, when the enrichment of at least one negative factor microorganism described above is a predetermined level or higher, the patient may be evaluated as having a negative treatment response to the treatment of cancer immunotherapy.

According to the above procedure, the method for predicting the treatment response according to an exemplary embodiment of the present invention may provide information so as to predict early the treatment response of the patient to cancer immunotherapy, particularly anti-PD-1 by measuring the levels of various microbial biomarkers including the TANB77 strain.

Evaluation 1: Establishment of Biomarker for Predicting Treatment Response to PD-1/PD-L1 Blocker_Severance Cohort Hereinafter, with reference to FIGS. 2A to 2F, biomarkers used in various exemplary embodiments of the present invention, particularly biomarkers capable of predicting an anti-PD-1 treatment response for patients at a basal level, and a method for predicting a treatment response using the same will be described.

In the experiment, data of 49 non-small cell lung cancer patients who received a PD-1 inhibitor at the Yonsei University Severance Hospital Cancer Center were used. More specifically, the relative abundance of taxa of intestinal microbiome including a TANB77 strain was evaluated by performing whole metagenome sequencing (WMS) analysis with respect to a fecal sample obtained from the lung cancer patient before receiving first anti-PD-1 treatment. In this case, the relative abundance may be a value obtained by dividing the number of reads aligned in each taxon by the total number of reads aligned, and each patient was classified as a responder group or a non-responder group for an anti-PD-1 treatment response based on chest posterior-anterior radiography or computed tomography.

Figure 2A:
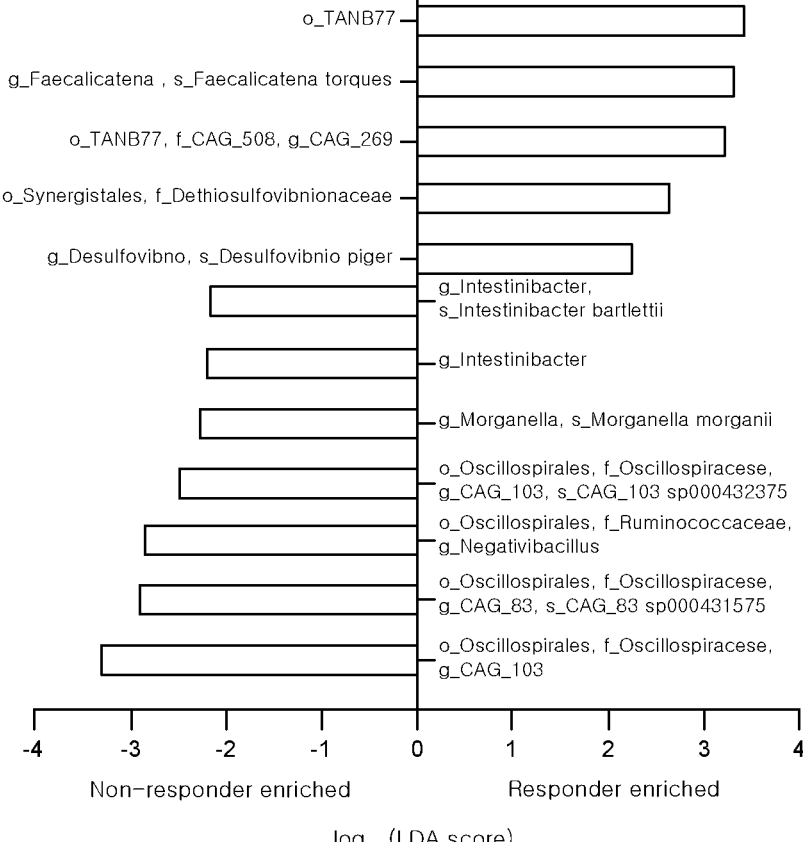
FIGS. 2A and 2B illustrate microorganisms with high enrichment among intestinal microbiome according to an anti-PD-1 treatment response.
Figure 2B:
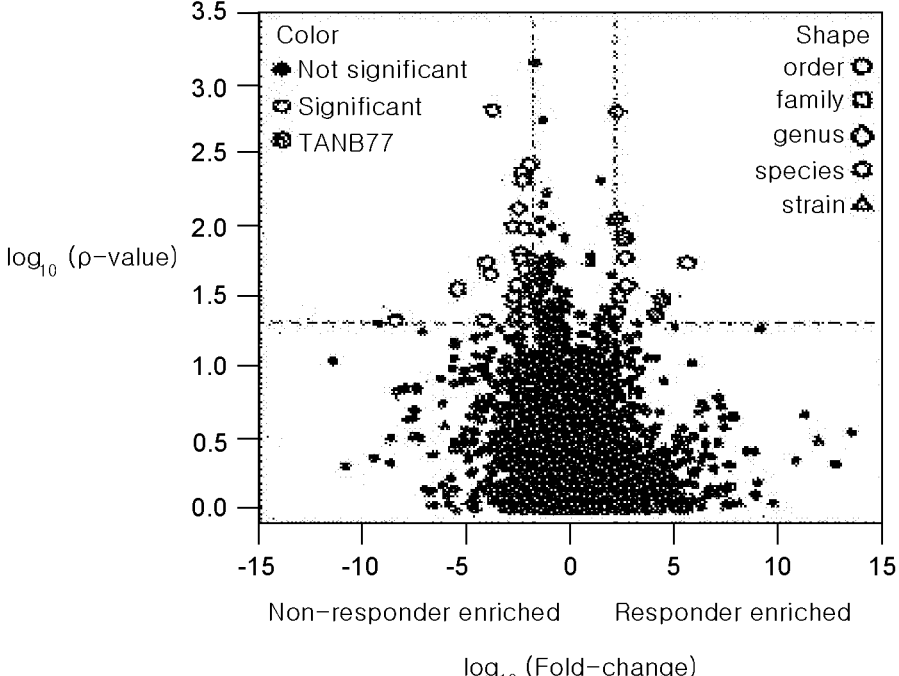
Figure 2C:
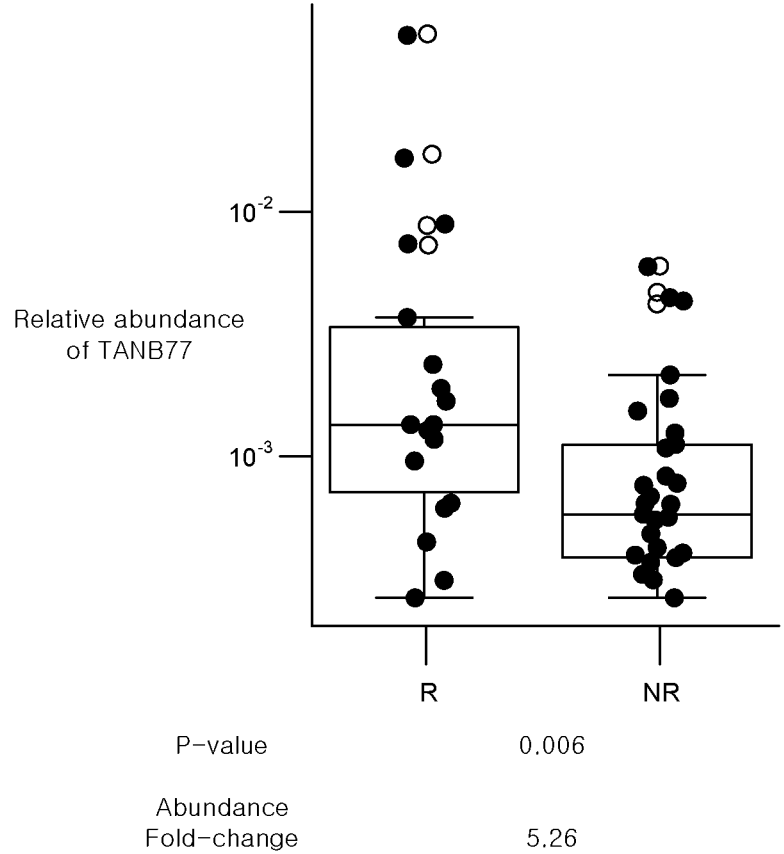
FIG. 2C illustrates an abundance of TANB77 according to an anti-PD-1 treatment response.
Figure 2D:
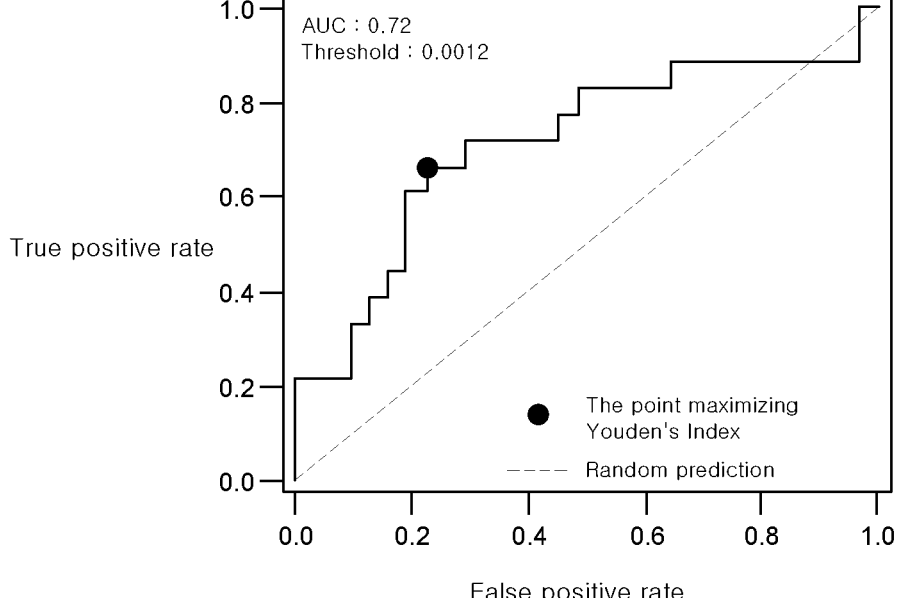
FIG. 2D shows a receiver operating characteristic (ROC) curve for anti-PD-1 treatment response prediction based on an abundance of TANB77 taxa used in various exemplary embodiments of the present invention.
Figure 2E:
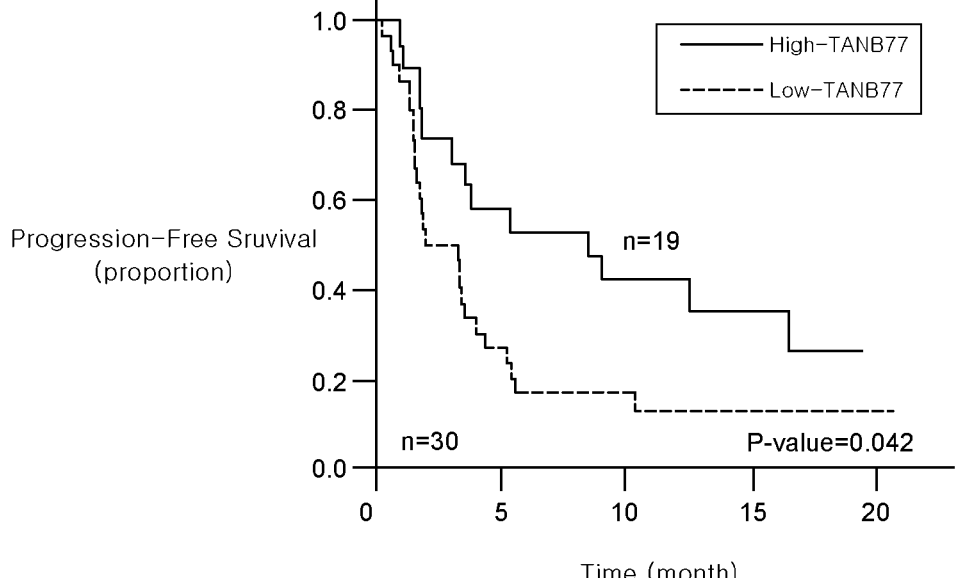
FIG. 2E illustrates results of analyzing a progression-free survivor (PFS) based on an abundance of the TANB77 taxa used in various exemplary embodiments of the present invention.
Figure 2F:
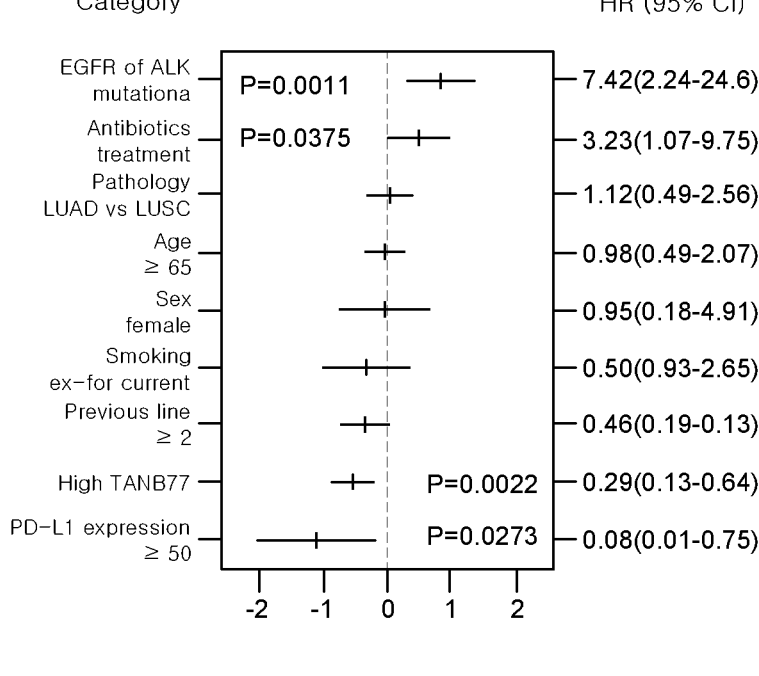
FIG. 2F shows a hazard ratio (HR) analysis result for various anti-PD-1 treatment response prediction parameters including an abundance of TANB77 taxa used in various exemplary embodiments of the present invention.

First, FIGS. 2A and 2B illustrate microorganisms with high enrichment among intestinal microbiome according to an anti-PD-1 treatment response. FIG. 2C illustrates an abundance of TANB77 according to an anti-PD-1 treatment response. FIG. 2D shows a receiver operating characteristic (ROC) curve for anti-PD-1 treatment response prediction based on an abundance of TANB77 taxa used in various exemplary embodiments of the present invention. FIG. 2E illustrates results of analyzing a progression-free survivor (PFS) based on the abundance of the TANB77 taxa used in various exemplary embodiments of the present invention. FIG. 2F shows a hazard ratio (HR) analysis result for various anti-PD-1 treatment response prediction parameters including an abundance of TANB77 taxa used in various exemplary embodiments of the present invention.

First, referring to FIG. 2A, according to a result of linear discriminant analysis using LefSe, as |LDA score|>2, responder enriched taxa among intestinal microbiome in the responder group were represented by TANB77, *Faecalicatena torques* species, CAG_269 genus, *Dethiosulfovibrio naceae* family, and *Desulfovibrio piger* species.

In contrast, as |LDA score|>2, non-responder enriched taxa among the intestinal microbiome of the non-responder group were represented by *Intestinibacter bartlettii* species,

*Intestinibacter* genus, *Morganella morganii* species, CAG_103 species, and CAG 83 species.

Furthermore, referring to FIG. 2B, among the taxa, particularly a TANB77 strain had significantly high enrichment in the responder group to anti-PD-1 treatment.

In other words, these results showed that there were differences in taxa with high enrichment among the intestinal microbiome depending on the response to cancer immunotherapy, particularly anti-PD-1 treatment, and particularly, the TANB77 strain had high enrichment in the responder group to the anti-PD-1 treatment. That is, the results may mean that the TANB77 strain may be used as a biomarker for predicting the anti-PD-1 treatment response.

In particular, referring to FIG. 2C, the relative abundance of TANB77 in a responder (R) group was 5.26 times higher than that in a non-responder (NR) group.

Referring to FIG. 2D, as a result of performing ROC analysis on the responder group according to the relative abundance of TANB77, AUC was 0.72.

These results may mean that the ratio of the TANB77 clade in the gut microbiota predicts the response to anti-PD-1 treatment with high accuracy.

Referring further to FIG. 2E, a high-TANB77 group (High-TANB77) and a low-TANB77 group (Low-TANB77) were divided based on 0.0012 (0.12%), which was a threshold of the relative abundance of TANB77 defined based on a Youden's Index in the above-described ROC curve, and then the results of performing progression-free survivor (PFS) analysis were illustrated.

More specifically, among 49 patients, a progression-free survival period for 19 patients classified as the high-TANB77 group was significantly high.

Referring to FIG. 2F, multivariate cox-regression results for multiple categories including PD-L1 expression used as a biomarker for predicting a treatment response to anti-PD-1 treatment and the enrichment of TANB77 were illustrated.

More specifically, according to the results of cox-regression analysis, TANB77 was shown to be a statistically significant PFS coefficient and shown as a positive factor for PFS together with the PD-L1 expression level.

As a result of Evaluation 1, it was confirmed that TANB77 taxa among various gut microbiota, a strain according to GTDB phylogenetic classification of at least one of CAG-269 sp000431335 species, CAG-465 sp000433135 species, CAG-465 sp000433335 species, CAG-269 sp001916055 species, CAG-465 sp000433755 species, CAG-793 sp000433915 species, CAG-492 sp000434015 species, CAG-452 sp000434035 species, CAG-245 sp000434195 species, CAG-492 sp000434335 species, CAG-245 sp000435175 species, CAG-273 sp003507395 species, CAG-269 sp000435535 species, CAG-273 sp000435755 species, CAG-269 sp001916065 species, CAG-269 sp000437215 species, CAG-354 sp001915925 species, CAG-273 sp000437855 species, CAG-269 sp003525075 species, CAG-269 sp000438255 species, CAG-273 sp000438355 species, CAG-269 sp001915995 species, CAG-269 sp001916005 species, CAG-269 sp001916035 species, UBA1234 sp002308995 species, CAG-452 sp002314935 species, CAG-269 sp002372935 species, CAG-793 sp002393975 species, UBA1234 sp002404755 species, UBA7001 sp002449785 species, CAG-492 sp002633185 species, CAG-269 sp003518755 species, CAG-273 sp003534295 species, CAG-269 genus, CAG-492 genus, CAG-793 genus, CAG-452 genus, CAG-245 genus, CAG-273 genus, CAG-354 genus, UBA7001 genus, CAG-465 genus, UBA1234 genus, CAG-508 family, CAG-465 family, and UBA1234 family according to GTDB phylogenetic classification, or a strain according to NCBI phylogenetic classification of at least one of phylogenetic classification IDs: 1262796, 1262847, 1262772, 1262800, 1262811, 1262840, 1262822, 1262810, 1262839, 1262813, 1262784, 1262841, 1262823, 1262815, 1262812, 1262807, 1262799, 1262820, 1262788, 1262801, 1262789, 1896989, 1896977, 1896978, 1896979, 1896980, 1896981, 1896986, 1950810, 1950830, 1950862, 1950880, 1950887, 1950920, 1958817, and 1506 according to NCBI phylogenetic classification may be used as a biomarker for predicting a treatment response in the prediction method for the treatment response according to various exemplary embodiments of the present invention. In particular, the strains may be used as a biomarker to predict the response to anti-PD-1 treatment before the anti-PD-1 treatment is performed, so that a quick treatment plan can be established for each patient.

Evaluation 2: Establishment of Biomarker for Predicting Treatment Response to PD-1/PD-L1 Blocker_Multiple Cohorts Hereinafter, with reference to FIGS. 3A to 3E, biomarkers used in various exemplary embodiments of the present invention, particularly biomarkers capable of predicting an anti-PD-1 treatment response for patients at a basal level, and a method for predicting a treatment response using the same will be described.

In the present experiment, there has been used data for patients with lung cancer, melanoma, and kidney cancer obtained from multiple cohorts for providing public data of a Peters cohort (Peters, B. A. et al. *Relating the gut metagenome and metatranscriptome to immunotherapy responses in melanoma patients. Genome Med* 11, 61, doi: 10.1186/s13073-019-0672-4 (2019)), a Gopalakrishnan cohort (Gopalakrishnan, V. et al. *Gut microbiome modulates response to anti-PD-1 immunotherapy in melanoma patients. Science* 359, 97-103, doi: 10.1126/science.aan4236 (2018)), a Matson cohort (Matson, V. et al. *The commensal microbiome is associated with anti-PD-1 efficacy in metastatic melanoma patients. Science* 359, 104-108, doi: 10.1126/science.aao3290 (2018)), a Frankel cohort (Frankel. A. E. et al. *Metagenomic Shotgun Sequencing and Unbiased Metabolomic Profiling Identify Specific Human Gut Microbiota and Metabolites Associated with Immune Checkpoint Therapy Efficacy in Melanoma Patients. Neoplasia* 19, 848-855, doi: 10.1016/j.neo.2017.08.004 (2017)), and a Routy cohort (Routy. B. et al. *Gut microbiome influences efficacy of PD-1-based immunotherapy against epithelial tumors. Science* 359, 91-97, doi: 10.1126/science.aan3706 (2018)). More specifically, in the experiment, in order to demonstrate the reproducibility of prediction of the anti-PD-1 treatment response based on TANB77, the evaluation in Evaluation 1 described above was performed on the data obtained from each of the multiple cohorts.

Figure 3A:
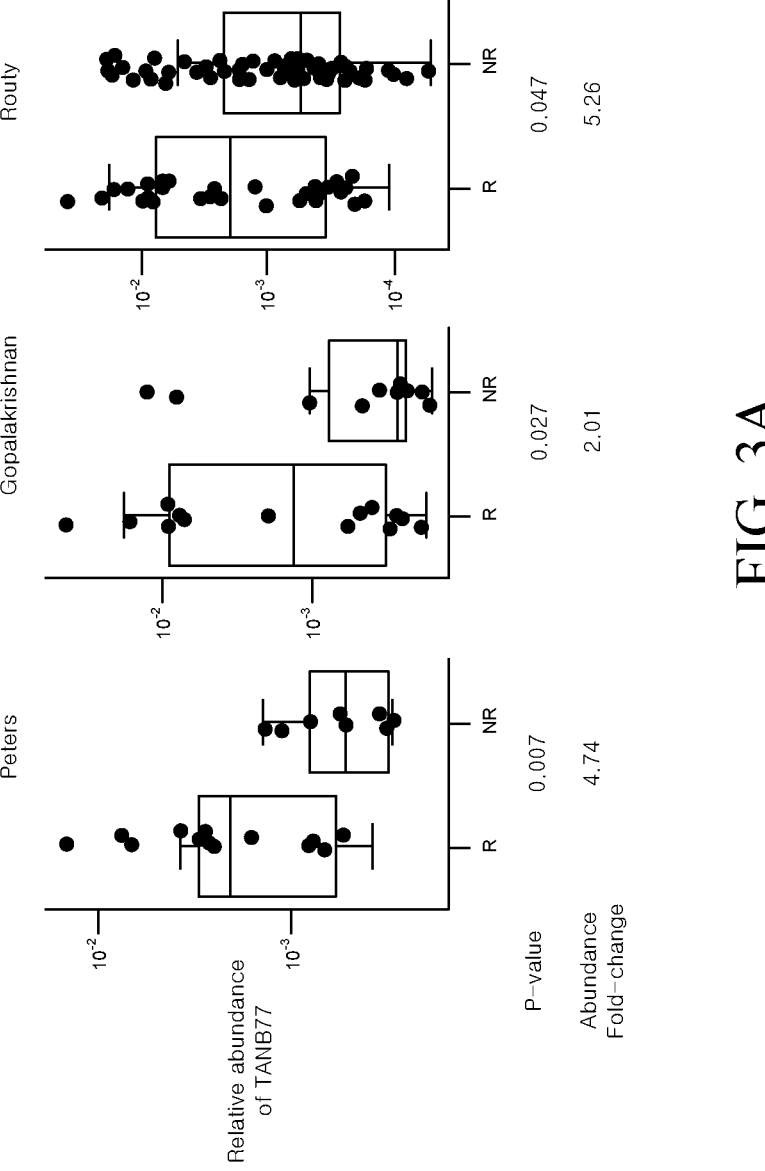
FIG. 3A illustrates an abundance of TANB77 according to an anti-PD-1 treatment response in multiple cohorts.
Figure 3B:
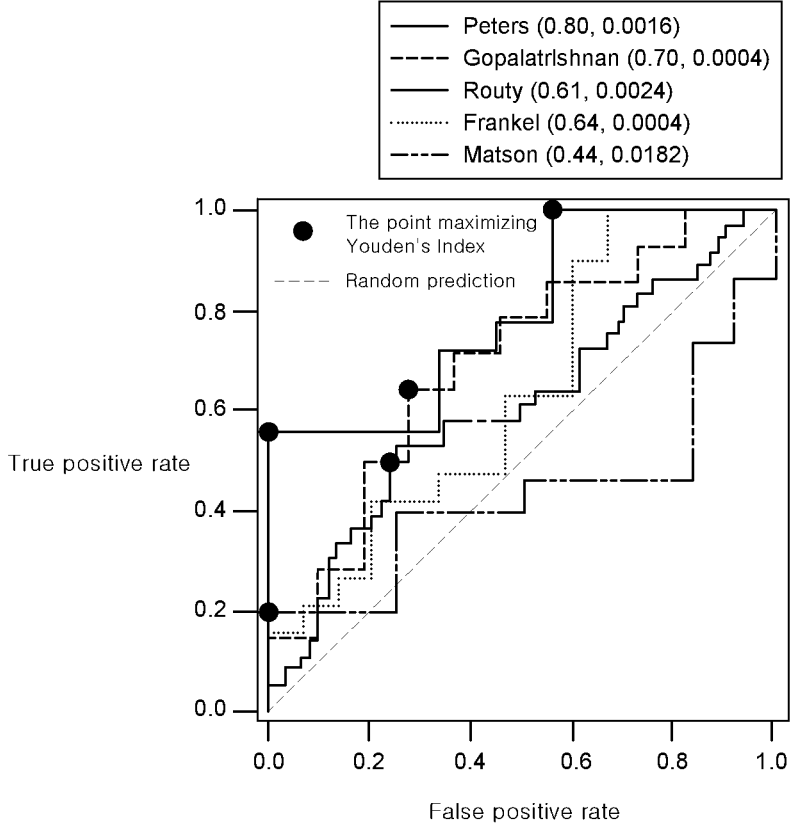
FIG. 3B shows a ROC curve for anti-PD-1 treatment response prediction based on an abundance of TANB77 taxa used in various exemplary embodiments of the present invention in multiple cohorts.
Figure 3C:
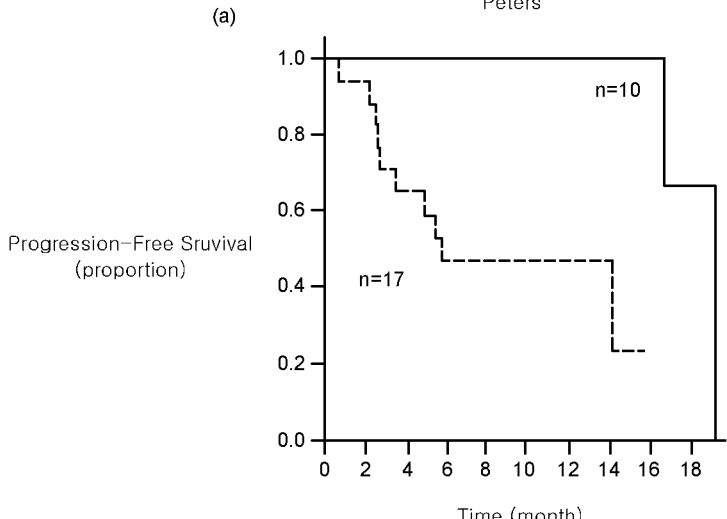
FIGS. 3C and 3D illustrate results of analyzing PFS based on an abundance of TANB77 taxa used in various exemplary embodiments of the present invention in multiple cohorts.
Figure 3C:
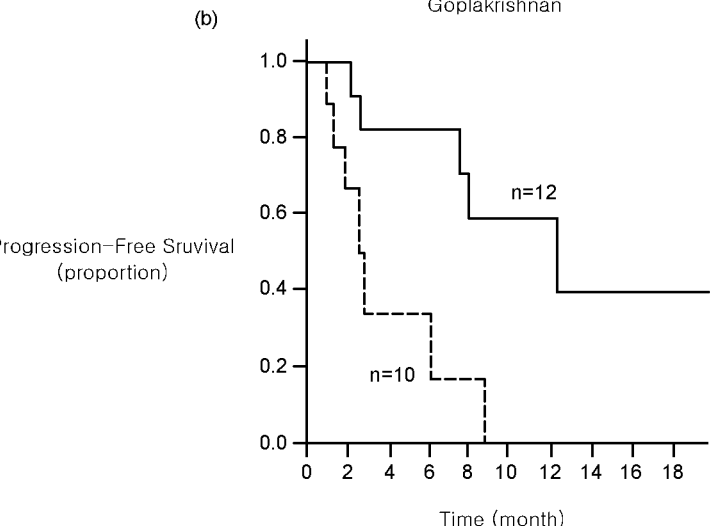
Figure 3D:
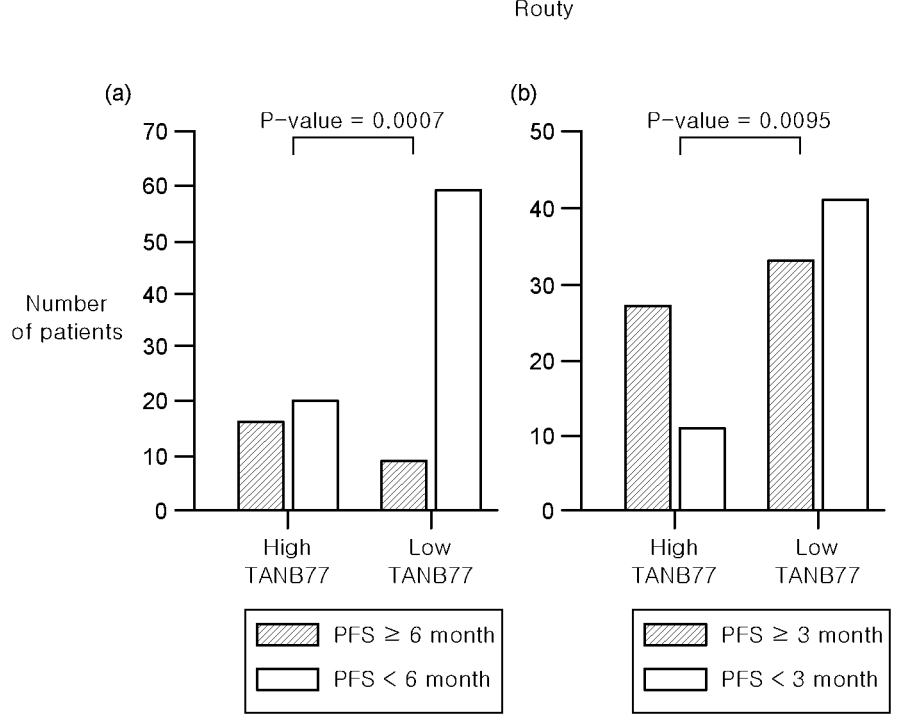
Figure 3E:
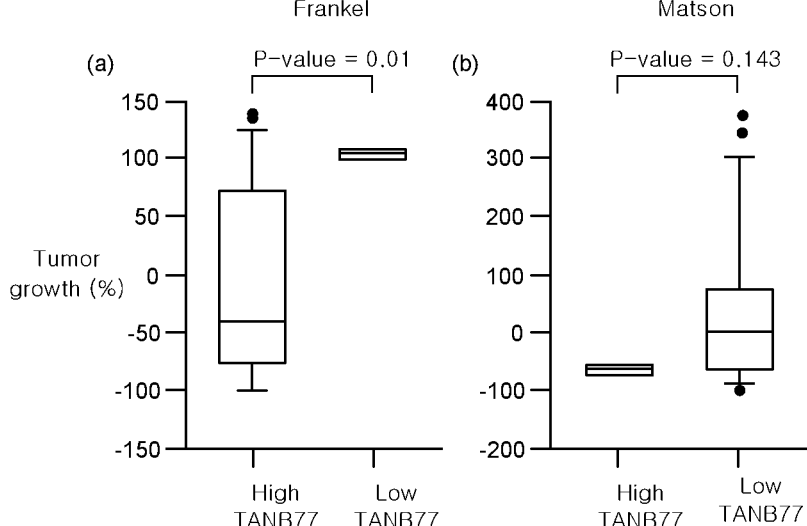
FIG. 3E illustrates a tumor growth rate based on an abundance of TANB77 taxa used in various exemplary embodiments of the present invention in a Routy cohort.

FIG. 3A illustrates an abundance of TANB77 according to an anti-PD-1 treatment response in multiple cohorts. FIG. 3B shows a ROC curve for anti-PD-1 treatment response prediction based on an abundance of TANB77 taxa used in various exemplary embodiments of the present invention in multiple cohorts. FIGS. 3C and 3D illustrate results of analyzing PFS based on an abundance of TANB77 taxa used in various exemplary embodiments of the present invention in multiple cohorts. FIG. 3E illustrates a tumor growth rate based on an abundance of TANB77 taxa used in various exemplary embodiments of the present invention in a Routy cohort.

First, referring to FIG. 3A, the relative abundance of TANB77 for the responder (R) group in the Peters cohort was 4.74 times higher than that for the non-responder (NR) group. In addition, the relative abundance of TANB77 for the responder (R) group in the Gopalakrishnan cohort was 2.01 times higher than that for the non-responder (NR) group. Furthermore, the relative abundance of TANB77 for the responder (R) group in the Routy cohort was 5.26 times higher than that for the non-responder (NR) group.

This may suggest that as the result of the Severance cohort described above in Evaluation 1, since the relative abundance of TANB77 has a significant difference between the responder group and the non-responder group, the TANB77 may be used as a biomarker for predicting the anti-PD-1 treatment response.

Next, referring to FIG. 3B, the results of performing ROC analysis on the responder group according to the relative abundance of TANB77 for each of the multiple cohorts are shown.

At this time, the AUC value for prediction of the treatment response according to the relative abundance of TANB77 in the Peters cohort was 0.80, the AUC value for prediction of the treatment response according to the relative abundance of TANB77 in the Gopalakrishnan cohort was 0.70, and the AUC value for predicting the treatment response according to the relative abundance of TANB77 in the Routy cohort was 0.61. In addition, the AUC value for predicting the treatment response according to the relative abundance of TANB77 in the Frankel cohort was 0.64.

These results may mean that the ratio of the TANB77 clade in the gut microbiota predicts the response to anti-PD-1 treatment with high accuracy.

Referring to FIG. 3C (a), a high-TANB77 group (High-TANB77) and a low-TANB77 group (Low-TANB77) were divided based on 0.0016 (0.16%), which was a threshold of the relative abundance of TANB77 defined based on a Youden's Index in the above-described ROC curve in the Peters cohort, and then the results of performing PFS analysis were illustrated.

More specifically, among 27 patients, a progression-free survival period for 10 patients classified as the high-TANB77 group was significantly higher than that of the low-TANB77 group.

Referring to FIG. 3C (b), a high-TANB77 group (High-TANB77) and a low-TANB77 group (Low-TANB77) were divided based on 0.0004 (0.04%), which was a threshold of the relative abundance of TANB77 defined based on a Youden's Index in the above-described ROC curve in the Gopalakrishnan cohort, and then the results of performing PFS analysis were illustrated.

More specifically, it was shown that among 22 patients, a progression-free survival period for 12 patients classified as the high-TANB77 group was significantly higher than that of the low-TANB77 group.

Referring to FIGS. 3D (a) and (b) together, the results of performing PFS analysis on the high-TANB77 group (High-TANB77) and the low-TANB77 group (Low-TANB77) in the Routy cohort were shown.

More specifically, it was shown that most patients in the low-TANB77 group had the PFS of less than 6 months. In addition, it was shown that 70% or more of patients in the high-TANB77 group had the PFS of 3 months or more.

These results may mean that the relative abundance of TANB77 is a positive factor for the PFS together with the PD-L1 expression level.

Next, referring to FIGS. 3E (a) and (b), it was shown that in the Frankel cohort and the Matson cohort, the tumor growth rate for the high-TANB77 group (High-TANB77)

was significantly lower than the tumor growth rate for the low-TANB77 group (Low-TANB77).

These results may also mean that the enrichment of TANB77 inhibits the tumor growth and induces a high treatment response to anti-PD-1 therapy.

As a result of Evaluation 2, it was confirmed that TANB77 may be used as a biomarker for predicting the treatment response in the method for predicting the treatment response according to various exemplary embodiments of the present invention.

In particular, by evaluating and comparing the enrichment of the TANB77 taxa from feces isolated from the patient before/after administration of new candidate prebiotics, candidate prebiotics for PD-1 treatment can be screened.

In addition, TANB77 may also be provided as a probiotics composition and a fecal microbiota transplantation composition for improving an anti-PD-1 treatment response.

For example, with respect to the feces isolated from the patient at each period before and after administration of prebiotics to increase the enrichment of the intestinal TANB77 strain which induces a high treatment response of PD-1/PD-L1 blockade therapy, the enrichment of TANB77 taxa may be evaluated, and the effect on candidate prebiotics may be evaluated based on the relative abundance of TANB77.

In addition, the microbiota containing TANB77 isolated from the feces of a patient with a positive anti-PD-1 treatment response may be transplanted into the intestine of a patient who intends to undergo cancer immunotherapy.

Evaluation 3: Establishment of Biomarker for Predicting Treatment Response to PD-1/PD-L1 Blocker_Bacterial Taxa Hereinafter, biomarkers of bacterial taxa for predicting a treatment response to a PD-1/PD-L1 blocker will be described in detail with reference to FIGS. 4A to 4D.

FIG. 4A lists microorganisms with relatively high enrichment among the intestinal microbiome of responders to anti-PD-1 treatment based on the Genome Taxonomy Database taxonomy (GTDB). FIG. 4B lists microorganisms with relatively high enrichment among the intestinal microbiome of non-responders to anti-PD-1 treatment based on GTDB classification. FIG. 4C lists microorganisms with relatively high enrichment among the intestinal microbiome of responders to anti-PD-1 treatment based on a Mann-Whitney U test. FIG. 4D lists microorganisms with relatively high enrichment among the intestinal microbiome of non-responders to anti-PD-1 treatment based on the Mann-Whitney U test.

First, referring to FIG. 4A, according to GTDB classification, *Faecalicatena torques* species, CAG_269 genus, *Dethiosulfovibrio naceae* family, and *Desulfovibrio piger* species including the TANB77 used in various exemplary embodiments of the present invention showed relatively higher enrichment in the intestinal microbiome of the responder group for the anti-PD-1 treatment than other strains.

Referring to FIG. 4B, according to GTDB classification, *Intestinibacter bartlettii* species, *Intestinibacter* genus, *Morganella morganii* species, CAG 103 sp000432375 species, *Negativibacillus* genus, and CAG 83 sp000431575 species showed relatively higher enrichment in the intestinal microbiome of the non-responder group for the anti-PD-1 treatment than other strains.

That is, these results may mean that in determining patients with a positive treatment response to cancer immunotherapy, particularly anti-PD-1 treatment, the relative abundance of *Faecalicatena torques* species, CAG_269 genus, *Dethiosulfovibrio naceae* family, and *Desulfovibrio piger* species, including TANB77 may be used as a biomarker.

Furthermore, these results may mean that in determining patients with a negative treatment response to anti-PD-1 treatment, the relative abundance of *Intestinibacter bartlettii* species, *Intestinibacter* genus, *Morganella morganii* species, CAG 103 sp000432375 species, *Negativibacillus* genus, and CAG 83 sp000431575 species may be used as a biomarker.

Referring to FIG. 4C, according to the Mann-Whitney U test, it was shown that CAG-274 family, CAG-508 family, CAG-521 genus, *Mailhella* genus, UBA3700 family, CAG-273 sp000438355 species, *Risungbinella* genus, Thermoactinomycetaceae family, *Risungbinella massiliensis* species, and CAG-245 genus had relatively higher enrichment in the intestinal microbiome of the responder group for the anti-PD-1 treatment than other strains.

Furthermore, referring to FIG. 4D, according to the Mann-Whitney U test, it was shown that CAG 103 genus, Rs-D84 genus, CAG-873 genus, *Collinsella* genus, *Butyricicoccus* genus, *Pseudescherichia* genus, *Yersinia mollaretii* species, *Campylobacter* fetus_A species, *Paenibacillus_F* sp000411255 species, *Paenibacillus_F* genus, *Pseudescherichia* sp002298805 species, UBA1417 genus, CAG-103 genus, *Leptotricia wadei* species, *Pantoea vagans_A* species, *Kurthia massiliensis* species, CAG-103 sp000432375 species, *Kurthia* genus, *Akkermansia* genus, *Porphyromonas somerae_A* species, *Ezakiella massiliensis* species, *Enterococcus_B faecium_B* species, *Bacteroides* A genus, CAG-727 family, *Nissabacter archeti* species, UBA71 genus, *Morganella morganii* A species, *Nissabacter* genus, *Yersinia kristensenii* species, and *Anaerococcus lactolyticus* species had relatively higher enrichment in the intestinal microbiome of the non-responder group for the anti-PD-1 treatment than other strains.

That is, these results may mean that in determining patients with a positive treatment response to cancer immunotherapy, particularly anti-PD-1 treatment, the relative abundance of CAG-274 family, CAG-508 family, CAG-521 genus, *Mailhella* genus, UBA3700 family, CAG-273 sp000438355 species, *Risungbinella* genus, Thermoactinomycetaceae family, *Risungbinella massiliensis* species, and CAG-245 genus as well as TANB77 may be used as a biomarker.

Furthermore, these results may mean that in determining patients with a negative treatment response to cancer immunotherapy, particularly anti-PD-1 treatment, the relative abundance of CAG 103 genus, Rs-D84 genus, CAG-873 genus, *Collinsella* genus, *Butyricicoccus* genus, *Pseudescherichia* genus, *Yersinia mollaretii* species, *Campylobacter fetus* A species, *Paenibacillus_F* sp000411255 species, *Paenibacillus_F* genus, *Pseudescherichia* sp002298805 species, UBA1417 genus, CAG-103 genus, *Leptotricia wadei* species, *Pantoea vagans_A* species, *Kurthia massiliensis* species, CAG-103 sp000432375 species, *Kurthia* genus, *Akkermansia* genus, *Porphyromonas somerae_A* species, *Ezakiella massiliensis* species, *Enterococcus_B faecium_B* species, *Bacteroides* A genus, CAG-727 family, *Nissabacter archeti* species, UBA71 genus, *Morganella morganii* A species, *Nissabacter* genus, *Yersinia kristensenii* species, and *Anaerococcus lactolyticus* species may be used as a biomarker.

According to Evaluation 3 above, the present invention can provide a plurality of biomarkers with high accuracy of prediction for a treatment response with respect to the feces obtained from the patient before the anti-PD-1 treatment is performed.

Accordingly, according to the present invention, it is possible to provide information that may be effective for early diagnosis, rather than a conventional method for predicting a response to anti-PD-1 treatment based on biomarkers, which had predicted responders and non-responders after primary treatment.

In addition, according to the present invention, it is possible to easily select an effective treatment according to whether a treatment response to the patient is positive or negative by accurately and rapidly providing the response to the anti-PD-1 treatment.

According to the present invention, it is possible to provide information to predict a treatment response for patients suspected of having various cancers to which anti-PD-1 treatment may be applied. For example, according to the present invention, it is possible to provide information on a treatment response to anti-PD-1 treatment for patients suspected of having non-small cell lung cancer, skin melanoma, head and neck cancer, stomach cancer, liver cancer, bone cancer, pancreatic cancer, skin cancer, uterine cancer, ovarian cancer, rectal cancer, colorectal cancer, colon cancer, breast cancer, uterine sarcoma, fallopian tube carcinoma, endometrial carcinoma, cervical carcinoma, vaginal carcinoma, vulvar carcinoma, esophageal cancer, laryngeal cancer, small intestine cancer, thyroid cancer, parathyroid cancer, sarcoma of the soft tissue, urethral cancer, penile cancer, prostate cancer, chronic or acute leukemia, childhood solid tumor, differentiated lymphoma, bladder cancer, kidney cancer, renal cell carcinoma, renal pelvic carcinoma, primary central nervous system lymphoma, spinal cord tumor, brainstem glioma, or pituitary adenoma.

Evaluation 4: Phylogenetic Classification Analysis of TANB77 Strain

Hereinafter, with reference to FIGS. 5A and 5B, a phylogenetic classification analysis result of a TANB77 strain will be described.

FIGS. 5A and 5B illustrate results of phylogenetic classification based on GTDB classification and NCBI classification for a TANB77 strain used in various exemplary embodiments of the present invention.

In various exemplary embodiments of the present invention, the TANB77 strain, which is provided as a biomarker for predicting the treatment response to cancer immunotherapy, is classified as *Clostridium* genus according to NCBI phylogenetic classification analysis, a traditional bacterial classification system.

Meanwhile, according to phylogenetic classification analysis based on recently constructed GTDB, it was shown that TANB77 was allocated as 'TANB77'.

In particular, the TANB77 strain has a remarkably small-sized genome compared to *Clostridium* genus, so that the TANB77 strain may be phylogenetically distinguished from *Clostridium* genus.

The features of various exemplary embodiments of the present invention can be partially or entirely coupled or combined with each other and can be interlocked and operated in technically various ways to be sufficiently appreciated by those skilled in the art, and the exemplary embodiments can be implemented independently of or in association with each other.

Although the exemplary embodiments of the present invention have been described in detail with reference to the accompanying drawings, the present invention is not limited thereto and may be embodied in many different forms without departing from the technical concept of the present invention. Therefore, the exemplary embodiments of the present invention are provided for illustrative purposes only but are not intended to limit the technical concept of the present invention. The scope of the technical concept of the present invention is not limited thereto. Therefore, it should be understood that the above-described exemplary embodiments are illustrative in all aspects and do not limit the present invention. The protective scope of the present invention should be construed based on the appended claims, and all the technical spirits in the equivalent scope thereof should be construed as falling within the scope of the present invention.

The invention claimed is:

1. A method for generating microbial taxonomic profile data for predicting a treatment response to cancer immunotherapy, comprising:

performing metagenomic sequencing on a fecal sample from a patient to generate the microbial taxonomic profile data; wherein the cancer immunotherapy is anti-PD-1 treatment, wherein the microbial taxonomic profile data shows enrichment in the fecal sample from the patient of the order TANB77, phylogenetically distinct from the *Clostridium* genus, Clostridiales or Clostridia class, according to Genome Taxonomy Database (GTDB) phylogenetic classification or taxa belonging to the order TANB77, or a strain according to the GTDB phylogenetic classification of at least one CAG-269 sp000431335 species, CAG-465 sp000433135 species, CAG-465 sp000433335 species, CAG-269 sp001916055 species, CAG-465 sp000433755 species, CAG-793 sp000433915 species, CAG-492 sp000434015 species, CAG-452 sp000434035 species, CAG-245 sp000434195 species, CAG-492 sp000434335 species, CAG-245 sp000435175 species, CAG-273 sp003507395 species, CAG-269 sp000435535 species, CAG-273 sp000435755 species, CAG-269 sp001916065 species, CAG-269 sp000437215 species, CAG-354 sp001915925 species, CAG-273 sp000437855 species, CAG-269 sp003525075 species, CAG-269 sp000438255 species, CAG-273 sp000438355 species, CAG-269 sp001915995 species, CAG-269 sp001916005 species, CAG-269 sp001916035 species, UBA1234 sp002308995 species, CAG-452 sp002314935 species, CAG-269 sp002372935 species, CAG-793 sp002393975 species, UBA1234 sp002404755 species, UBA7001 sp002449785 species, CAG-492 sp002633185 species, CAG-269 sp003518755 species, CAG-273 sp003534295 species, CAG-269 genus, CAG-492 genus, CAG-793 genus, CAG-452 genus, CAG-245 genus, CAG-273 genus, CAG-354 genus, UBA7001 genus, CAG-465 genus, UBA1234 genus, CAG-508 family, CAG-465 family, or UBA1234 family according to the GTDB phylogenetic classification;

wherein the enrichment of the order TANB77 or the taxa, or the at least one strain according to the GTDB phylogenetic classification is a biomarker for predicting the treatment response to the anti-PD-1 treatment, and wherein the fecal sample includes gut microbiota.

2. The method for generating microbial taxonomic profile data for predicting the treatment response to cancer immunotherapy of claim 1, wherein the fecal sample includes feces isolated from the patient before the anti-PD-1 treatment is performed.

3. The method for generating microbial taxonomic profile data for predicting the treatment response to cancer immunotherapy of claim 1, wherein the microbial taxonomic profile data comprises a relative abundance of the order TANB77, the taxa, or the at least one strain according to the GTDB phylogenetic classification in the gut microbiota, and wherein the relative abundance at a predetermined level or higher is a biomarker for a positive treatment response.

4. The method for generating microbial taxonomic profile data for predicting the treatment response to cancer immunotherapy of claim 3, wherein the microbial taxonomic profile data comprises the enrichment of the order TANB77 or the taxa, and wherein the predetermined level of the relative abundance of the order TANB77 or the taxa is 0.01% to 0.5%.

5. The method for generating microbial taxonomic profile data for predicting the treatment response to cancer immunotherapy of claim 1, wherein the microbial taxonomic profile data shows enrichment in the fecal sample from the patient of the order TANB77 or the taxa, and the enrichment of at least one additional strain of *Faecalicatena torques* species, CAG 269 genus, *Dethiosulfovibrio naceae* family, *Desulfovibrio piger* species, CAG-274 family, CAG-508 family, CAG-521 genus, *Mailhella* genus, UBA3700 family, CAG-273 sp000438355 species, *Risungbinella* genus, Thermoactinomycetaceae family, *Risungbinella massiliensis* species, or CAG-245 genus according to the GTDB phylogenetic classification; and wherein the enrichment of the order TANB77 or the taxa, and the at least one additional strain is a biomarker for predicting the treatment response to the anti-PD-1 treatment.

6. The method for generating microbial taxonomic profile data for predicting the treatment response to cancer immunotherapy of claim 5, wherein the enrichment of the order TANB77 or the taxa, and the at least one additional strain at a predetermined level or higher is a biomarker for a positive treatment response.

7. The method for generating microbial taxonomic profile data for predicting the treatment response to cancer immunotherapy of claim 1, wherein the microbial taxonomic profile data shows enrichment in the fecal sample from the patient of at least one additional strain of *Intestinibacter bartlettii* species, *Intestinibacter* genus, *Morganella morganii* species, CAG 103 sp000432375 species, *Negativibacillus* genus, CAG 83 sp000431575 species, CAG 103 genus, Rs-D84 genus, CAG-873 genus, *Collinsella* genus, *Butyricicoccus* genus, *Pseudescherichia* genus, *Yersinia mollaretii* species, *Campylobacter* fetus_A species, *Paenibacillus*_F sp000411255 species, *Paenibacillus*_F genus, *Pseudescherichia* sp002298805 species, UBA1417 genus, CAG-103 genus, *Leptotricia wadei* species, *Pantoea vagans*_A species, *Kurthia massiliensis* species, CAG-103 sp000432375 species, *Kurthia* genus, *Akkermansia* genus, *Porphyromonas somerae*_A species, *Ezakiella massiliensis* species, *Enterococcus*_B *faecium*_B species, *Bacteroides* A genus, CAG-727 family, *Nissabacter archeti* species, UBA71 genus, *Morganella morganii* A species, *Nissabacter* genus, *Yersinia kristensenii* species, or *Anaerococcus lactolyticus* species according to the GTDB phylogenetic classification; and wherein the enrichment of the at least one additional strain is a biomarker for predicting the treatment response to the anti-PD-1 treatment.

8. The method for generating microbial taxonomic profile data for predicting the treatment response to cancer immunotherapy of claim 7, wherein the enrichment of the at least one additional strain at a predetermined level or higher is a biomarker for a negative treatment response.

9. The method for generating microbial taxonomic profile data for predicting the treatment response to cancer immunotherapy of claim 1, wherein the patient is a patient suspected of having at least one disease selected from the group consisting of non-small cell lung cancer, skin melanoma, head and neck cancer, stomach cancer, liver cancer, bone cancer, pancreatic cancer, skin cancer, uterine cancer, ovarian cancer, rectal cancer, colorectal cancer, colon cancer, breast cancer, uterine sarcoma, fallopian tube carcinoma, endometrial carcinoma, cervical carcinoma, vaginal carcinoma, vulvar carcinoma, esophageal cancer, laryngeal cancer, small intestine cancer, thyroid cancer, parathyroid cancer, sarcoma of the soft tissue, urethral cancer, penile cancer, prostate cancer, chronic or acute leukemia, childhood solid tumor, differentiated lymphoma, bladder cancer, kidney cancer, renal cell carcinoma, renal pelvic carcinoma, primary central nervous system lymphoma, spinal cord tumor, brainstem glioma, and pituitary adenoma.

10. A method for generating microbial taxonomic profile data for predicting a treatment response to cancer immunotherapy comprising:

performing metagenomic sequencing on a fecal sample from a patient to generate the microbial taxonomic profile data; wherein the cancer immunotherapy is anti-PD-1 treatment, wherein the microbial taxonomic profile data shows enrichment in the fecal sample from the patient of a strain according to NCBI (National Center for Biotechnology Information) phylogenetic classification of at least one of phylogenetic classification IDs: 1262796, 1262847, 1262772, 1262800, 1262811, 1262840, 1262822, 1262810, 1262839, 1262813, 1262784, 1262841, 1262823, 1262815, 1262812, 1262807, 1262799, 1262820, 1262788, 1262801, 1262789, 1896989, 1896977, 1896978, 1896979, 1896980, 1896981, 1896986, 1950810, 1950830, 1950862, 1950880, 1950887, 1950920, 1958817, or 1506 according to the NCBI phylogenetic classification; and wherein the enrichment of the at least one strain according to the NCBI phylogenetic classification is a biomarker for predicting the treatment response to the anti-PD-1 treatment.

11. The method for generating microbial taxonomic profile data for predicting the treatment response to cancer immunotherapy of claim 10, wherein the microbial taxonomic profile data shows enrichment in the fecal sample from the patient of at least one additional strain of *Faecalicatena torques* species, CAG 269 genus, *Dethiosulfovibrio naceae* family, *Desulfovibrio piger* species, CAG-274 family, CAG-508 family, CAG-521 genus, *Mailhella* genus, UBA3700 family, CAG-273 sp000438355 species, *Risungbinella* genus, Thermoactinomycetaceae family, *Risungbinella massiliensis* species, or CAG-245 genus according to GTDB phylogenetic classification; and wherein the enrichment of the strain according to the NCBI phylogenetic classification and the enrichment of the at least one additional strain are a biomarker for predicting the treatment response to the anti-PD-1 treatment.

12. The method for generating microbial taxonomic profile data for predicting the treatment response to cancer immunotherapy of claim 10, wherein the microbial taxonomic profile data shows enrichment in the fecal sample from the patient of at least one additional strain of *Intestinibacter bartlettii* species, *Intestinibacter* genus, *Morganella morganii* species, CAG 103 sp000432375 species, *Negativibacillus* genus, CAG 83 sp000431575 species, CAG 103 genus, Rs-D84 genus, CAG-873 genus, *Collinsella* genus, *Butyricicoccus* genus, *Pseudescherichia* genus, *Yersinia mollaretii* species, *Campylobacter* fetus_A species, *Paenibacillus*_F sp000411255 species, *Paenibacillus*_F genus, *Pseudescherichia* sp002298805 species, UBA1417 genus, CAG-103 genus, *Leptotricia wadei* species, *Pantoea vagans*_A species, *Kurthia massiliensis* species, CAG-103 sp000432375 species, *Kurthia* genus, *Akkermansia* genus, *Porphyromonas somerae*_A species, *Ezakiella massiliensis* species, *Enterococcus*_B *faecium*_B species, *Bacteroides* A genus, CAG-727 family, *Nissabacter archeti* species, UBA71 genus, *Morganella morganii* A species, *Nissabacter* genus, *Yersinia kristensenii* species, or *Anaerococcus lactolyticus* species according to GTDB phylogenetic classification; and wherein the enrichment of the at least one additional strain is a biomarker for predicting the treatment response to the anti-PD-1 treatment.

13. A method for screening candidate prebiotics comprising:

performing metagenomic sequencing on a fecal sample from a patient to generate microbial taxonomic profile data, wherein the patient has not received the candidate prebiotics;

wherein the microbial taxonomic profile data shows enrichment in the fecal sample from the patient of the order TANB77 according to GTDB phylogenetic classification or taxa belonging to the order TANB77, or a strain according to GTDB phylogenetic classification of at least one of CAG-269 sp000431335 species, CAG-465 sp000433135 species, CAG-465 sp000433335 species, CAG-269 sp001916055 species, CAG-465 sp000433755 species, CAG-793 sp000433915 species, CAG-492 sp000434015 species, CAG-452 sp000434035 species, CAG-245 sp000434195 species, CAG-492 sp000434335 species, CAG-245 sp000435175 species, CAG-273 sp003507395 species, CAG-269 sp000435535 species, CAG-273 sp000435755 species, CAG-269 sp001916065 species, CAG-269 sp000437215 species, CAG-354 sp001915925 species, CAG-273 sp000437855 species, CAG-269 sp003525075 species, CAG-269 sp000438255 species, CAG-273 sp000438355 species, CAG-269 sp001915995 species, CAG-269 sp001916005 species, CAG-269 sp001916035 species, UBA1234 sp002308995 species, CAG-452 sp002314935 species, CAG-269 sp002372935 species, CAG-793 sp002393975 species, UBA1234 sp002404755 species, UBA7001 sp002449785 species, CAG-492 sp002633185 species, CAG-269 sp003518755 species, CAG-273 sp003534295 species, CAG-269 genus, CAG-492 genus, CAG-793 genus, CAG-452 genus, CAG-245 genus, CAG-273 genus, CAG-354 genus, UBA7001 genus, CAG-465 genus, UBA1234 genus, CAG-508 family, CAG-465 family, or UBA1234 family according to the GTDB phylogenetic classification, before administering the candidate prebiotics;

administering the candidate prebiotics; and performing an additional metagenomic sequencing on a fecal sample from the patient to generate microbial taxonomic profile data after the administering of the candidate prebiotics;

wherein the microbial taxonomic profile data shows differences in enrichment in the fecal sample from the patient of the order TANB77 or the taxa, or the at least one strain according to the GTDB phylogenetic classification before administering the candidate prebiotics with the enrichment of the order TANB77 or the taxa, or the at least one strain according to the GTDB phylogenetic classification after the administering of the candidate prebiotics; and wherein the candidate prebiotic increases the enrichment after the administration relative to before the administration.

* * * * *